(12) United States Patent
Jennings et al.

(10) Patent No.: US 11,371,033 B2
(45) Date of Patent: Jun. 28, 2022

(54) SUBTILASE CYTOTOXIN B SUBUNIT MUTANT

(71) Applicants: GRIFFITH UNIVERSITY, Nathan (AU); THE UNIVERSITY OF ADELAIDE, Adelaide (AU)

(72) Inventors: Michael Paul Jennings, Manly (AU); Christopher Day, Labrador (AU); Adrienne Webster Paton, Parkside (AU); James Cleland Paton, Parkside (AU)

(73) Assignees: Griffith University, Nathan (AU); The University of Adelaide, Adelaide (AU)

( * ) Notice: Subject to any disclaimer, the term of this patent is extended or adjusted under 35 U.S.C. 154(b) by 242 days.

(21) Appl. No.: 16/348,732

(22) PCT Filed: Nov. 9, 2017

(86) PCT No.: PCT/AU2017/051230
§ 371 (c)(1),
(2) Date: May 9, 2019

(87) PCT Pub. No.: WO2018/085888
PCT Pub. Date: May 17, 2018

(65) Prior Publication Data
US 2019/0367895 A1    Dec. 5, 2019

(30) Foreign Application Priority Data

Nov. 9, 2016 (AU) .................. 2016904572

(51) Int. Cl.
| | |
|---|---|
| *C12N 9/52* | (2006.01) |
| *C07K 16/40* | (2006.01) |
| *G01N 33/574* | (2006.01) |
| *A61K 38/00* | (2006.01) |

(52) U.S. Cl.
CPC .............. *C12N 9/52* (2013.01); *C07K 16/40* (2013.01); *C12Y 304/21062* (2013.01); *G01N 33/57492* (2013.01); *A61K 38/00* (2013.01); *C07K 2317/34* (2013.01); *G01N 2400/00* (2013.01)

(58) Field of Classification Search
CPC .......... C12N 9/54; C12N 15/00; C11D 3/386
See application file for complete search history.

(56) References Cited

U.S. PATENT DOCUMENTS 7,078,489 B2 *   7/2006  Paton ................ C12N 9/52
                                                530/350
2005/0136424 A1   6/2005  Paton et al.

FOREIGN PATENT DOCUMENTS

WO    2012/101235    8/2012

OTHER PUBLICATIONS

Tozzoli et al. 2010; Production of the subtilase AB5 cytotoxin by shiga toxin-negative *Escherichia coli*. Journal of Clinical Microbiology. 48(1): 178-183.*
Byres E. et al. "Incorporation of a non-human glycan mediates human susceptibility to a bacterial toxin" Nature (2008) 456(7222): 648-652.
Beddoe T. et al. "Structure, Biological Functions and Applications of the AB5 Toxins" Trends Biochem Sci. (2010) 35 (7): 411-418.
Day C.J. et al. "Structure aided design of a Neu5Gc specific lectin" Scientific Reports (2017) 7: 1495.
Funk J. et al. "Molecular analysis of subtilase cytotoxin genes of food-borne Shiga toxin-producing *Escherichia coli* reveals a new allelic SubAB variant" BMC Microbiology (2013) 13: 230.
Le Nours J. et al. "Structural Basis of Subtilase Cytotoxin SubAB Assembly" The Journal of Biological Chemistry (2013) 288 (38): 27505-27516.
Michelacci V. et al. "A new pathogenicity island carrying an allelic variant of the Subtilase cytotoxin is common among Shiga toxin producing *Escherichia coli* of human and ovine origin" Clin Microbiol Infect (2013) 19: E149-E156.
Paton A.W. et al., "A New Family of Potent AB5 Cytotoxins Produced by Shiga Toxigenic *Escherichia coli*" J. Exp. Med. (2004) 200 (1): 35-46.
Paton A.W. and Paton J.C. "*Escherichla coli* Subtilase Cytotoxin" Toxins (2010) 2: 215-228.
International Search Report and Written Opinion corresponding to International Application No. PCT/AU2017/051230 dated Jan. 18, 2018.

* cited by examiner

*Primary Examiner* — Karen Cochrane Carlson
(74) *Attorney, Agent, or Firm* — Myers Bigel, P.A.

(57) ABSTRACT

A mutant subtilase cytotoxin B subunit protein is provided which can bind glycans having α2-3-linked N-glycolylneuraminic acid and glycans having α2-6-linked N-glycolylneuraminic acid. The mutant SubB protein has deletions of one or more of the amino acid sequence TTSTE and has a previously undescribed ability to bind glycans having α2-6-linked N-glycolylneuraminic acid, while not losing the ability to bind glycans having α2-3-linked N-glycolylneuraminic acid.

16 Claims, 15 Drawing Sheets

Specification includes a Sequence Listing.

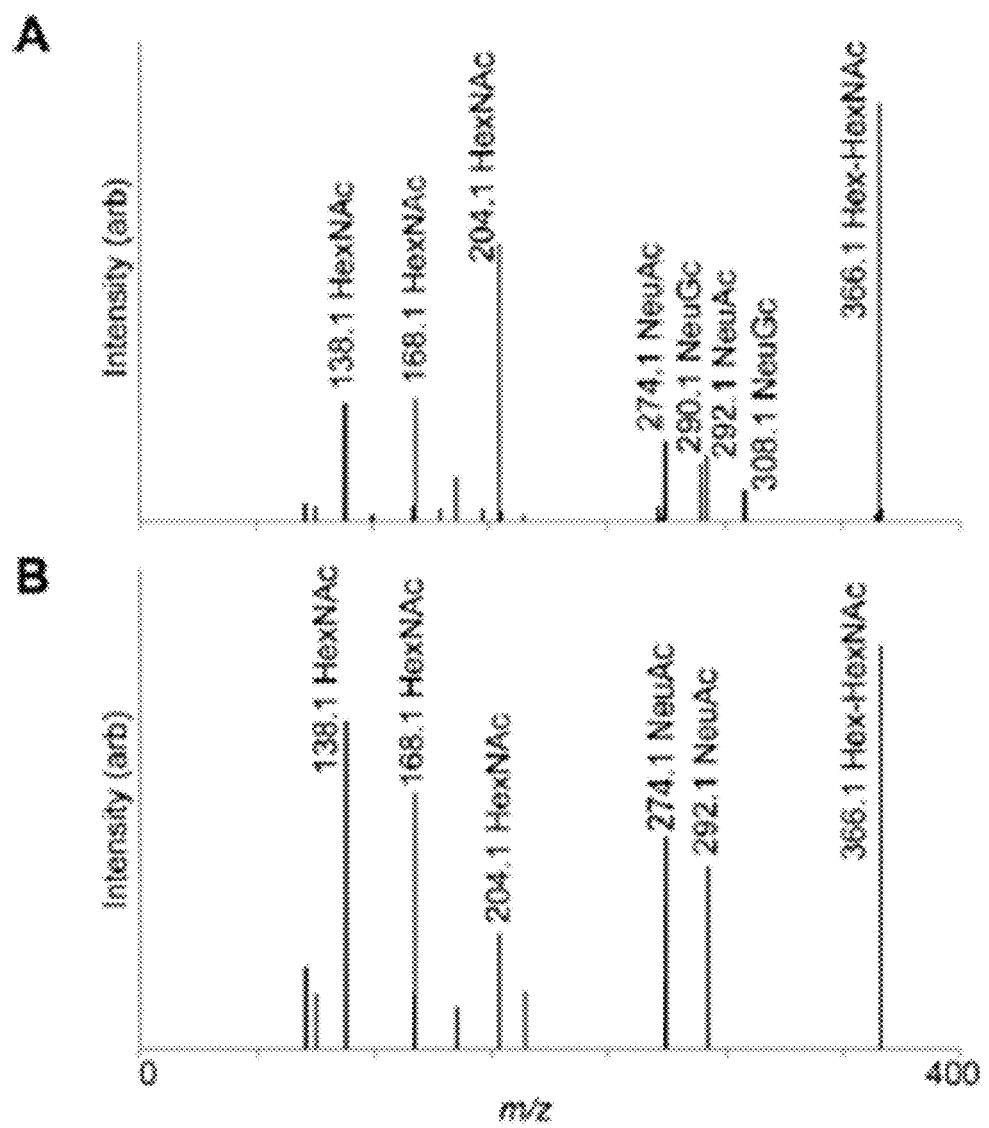
Figure 5A-B

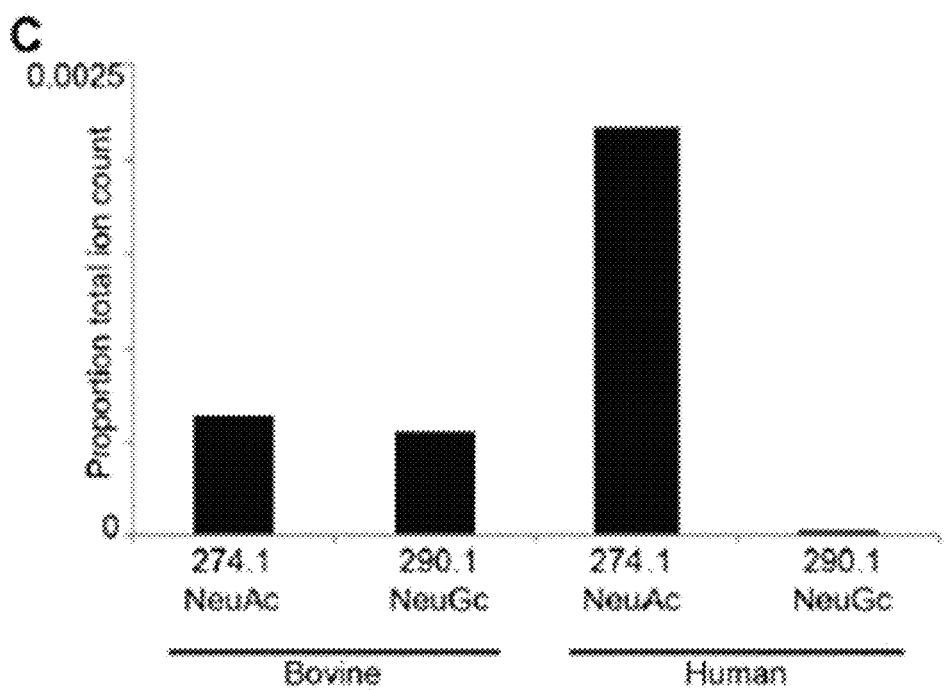
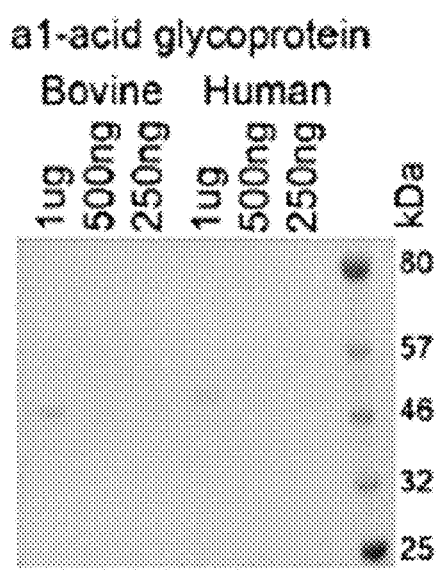
Figure 5C-D

SEQUENCE LISTING

<160> NUMBER OF SEQ ID NOS: 10

<210> SEQ ID NO 1
<211> LENGTH: 116
<212> TYPE: PRT
<213> ORGANISM: Escherichia coli

<400> SEQUENCE: 1

Glu Trp Thr Gly Asp Ala Arg Asp Gly Met Phe Ser Gly Val Val Ile
1               5                   10                  15

```
Thr Gln Phe His Thr Gly Gln Ile Asp Asn Lys Pro Tyr Phe Cys Ile
             20                  25                  30

Glu Gly Lys Gln Ser Ala Gly Ser Ser Ile Ser Ala Cys Ser Met Lys
         35                  40                  45

Asn Ser Ser Val Trp Gly Ala Ser Phe Ser Thr Leu Tyr Asn Gln Ala
     50                  55                  60

Leu Tyr Phe Tyr Thr Thr Gly Gln Pro Val Arg Ile Tyr Tyr Lys Pro
65                  70                  75                  80

Gly Val Trp Thr Tyr Pro Pro Phe Val Lys Ala Leu Thr Ser Asn Ala
                 85                  90                  95

Leu Val Gly Leu Ser Thr Cys Thr Thr Glu Cys Phe Gly Pro Asp Arg
            100                 105                 110

Lys Lys Asn Ser
        115
```

<210> SEQ ID NO 2
<211> LENGTH: 141
<212> TYPE: PRT
<213> ORGANISM: Escherichia coli

<400> SEQUENCE: 2

```
Met Thr Ile Lys Arg Phe Phe Val Cys Ala Gly Ile Met Gly Cys Leu
1               5                   10                  15

Ser Leu Asn Pro Ala Met Ala Glu Trp Thr Gly Asp Ala Arg Asp Gly
            20                  25                  30

Met Phe Ser Gly Val Val Ile Thr Gln Phe His Thr Gly Gln Ile Asp
         35                  40                  45

Asn Lys Pro Tyr Phe Cys Ile Glu Gly Lys Gln Ser Ala Gly Ser Ser
     50                  55                  60

Ile Ser Ala Cys Ser Met Lys Asn Ser Ser Val Trp Gly Ala Ser Phe
65                  70                  75                  80

Ser Thr Leu Tyr Asn Gln Ala Leu Tyr Phe Tyr Thr Thr Gly Gln Pro
                 85                  90                  95

Val Arg Ile Tyr Tyr Lys Pro Gly Val Trp Thr Tyr Pro Pro Phe Val
            100                 105                 110

Lys Ala Leu Thr Ser Asn Ala Leu Val Gly Leu Ser Thr Cys Thr Thr
         115                 120                 125

Ser Thr Glu Cys Phe Gly Pro Asp Arg Lys Lys Asn Ser
    130                 135                 140
```

<210> SEQ ID NO 3
<211> LENGTH: 5
<212> TYPE: PRT
<213> ORGANISM: Escherichia coli
<220> FEATURE:
<221> NAME/KEY: MISC_FEATURE
<222> LOCATION: (1)..(2)
<223> OTHER INFORMATION: Residue may be deleted.
<221> NAME/KEY: MISC_FEATURE
<222> LOCATION: (3)..(5)
<223> OTHER INFORMATION: Residue may be modified or deleted.

<400> SEQUENCE: 3

```
Thr Thr Ser Thr Glu
1               5
```

<210> SEQ ID NO 4
<211> LENGTH: 28
<212> TYPE: DNA
<213> ORGANISM: Escherichia coli -continued

```
<400> SEQUENCE: 4
ttgtaaggat ccggaggtgc atatgacg                                     28

<210> SEQ ID NO 5
<211> LENGTH: 65
<212> TYPE: DNA
<213> ORGANISM: Escherichia coli

<400> SEQUENCE: 5
gattatctcg agtgagttct ttttcctgtc aggaccaaaa cattctgccg atgtggtgca  60
ggttg                                                              65

<210> SEQ ID NO 6
<211> LENGTH: 65
<212> TYPE: DNA
<213> ORGANISM: Escherichia coli

<400> SEQUENCE: 6
gattatctcg agtgagttct ttttcctgtc aggaccaaaa cattctgccg ctgtggtgca  60
ggttg                                                              65

<210> SEQ ID NO 7
<211> LENGTH: 66
<212> TYPE: DNA
<213> ORGANISM: Escherichia coli

<400> SEQUENCE: 7
gattatctcg agtgagttct ttttcctgtc aggaccaaaa cattctgtgg tgcaggttga  60
taaccc                                                             66

<210> SEQ ID NO 8
<211> LENGTH: 66
<212> TYPE: DNA
<213> ORGANISM: Escherichia coli

<400> SEQUENCE: 8
gattatctcg agtgagttct ttttcctgtc aggaccaaaa cagtctgtgg tgcaggttga  60
taaccc                                                             66

<210> SEQ ID NO 9
<211> LENGTH: 12
<212> TYPE: PRT
<213> ORGANISM: Bos taurus
<220> FEATURE:
<221> NAME/KEY: CARBOHYD
<222> LOCATION: (9)..(9)
<223> OTHER INFORMATION: Hex2HexNAc2NeuAc1NeuGc1+Man3GlcNAc2

<400> SEQUENCE: 9

Thr Phe Met Leu Ala Ala Ser Trp Asn Gly Thr Lys
1               5                   10

<210> SEQ ID NO 10
<211> LENGTH: 15
<212> TYPE: PRT
<213> ORGANISM: Homo sapiens
<220> FEATURE:
<221> NAME/KEY: CARBOHYD
<222> LOCATION: (7)..(7)
<223> OTHER INFORMATION: Hex3HexNAc3NeuAc2+Man3GlcNAc2
```

```
<400> SEQUENCE: 10

Gln Asp Gln Cys Ile Tyr Asn Thr Thr Tyr Leu Asn Val Gln Arg
1               5                   10                  15
```

SUBTILASE CYTOTOXIN B SUBUNIT MUTANT

CROSS-REFERENCE TO RELATED APPLICATIONS

This application is a 35 U.S.C. § 371 national phase application of PCT Application PCT/AU2017/051230, filed Nov. 9, 2017, which claims the benefit of priority of Australian provisional application No. 2016904572, filed 9 Nov. 2016, the entire contents of each of which are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 9875-17_ST25.txt, 3,950 bytes in size, generated on May 9, 2019 and filed via EFS-Web, is provided in lieu of a paper copy. This Sequence Listing is hereby incorporated by reference into the specification for its disclosures.

TECHNICAL FIELD

THIS INVENTION relates to bacterial toxin proteins. More particularly, this invention relates to a mutant subtilise cytotoxin B subunit protein having an ability to bind α2-6-linked N-glycolylneuraminic acid while retaining the ability to bind α2-3-linked N-glycolylneuraminic acid.

BACKGROUND

AB5 toxins exert their effects in a two-step process: (i) binding of the pentameric B subunit to specific glycan receptors on the target cell surface; (ii) internalisation of the AB5 toxin, followed by A subunit-mediated inhibition or corruption of essential host functions[1]. The B subunits of AB5 toxins recognize cell surface glycan receptors, directing internalization and intracellular trafficking of the holotoxin. Specificity of these protein-glycan interactions is critical for pathogenesis, as it determines host susceptibility and tissue tropism. Moreover, the pentavalent interactions between AB5 toxin B subunits and their cognate glycans result in very high affinity binding, making them powerful ligands for glycan detection, a noteworthy example being use of the cholera toxin B subunit for detection of the ganglioside GM1 in histopathological sections[2] and for labelling of lipid rafts in membranes[3].

In 2004 Paton et al. described the discovery and initial biological characterization of a new sub-family of bacterial AB5 toxins with the prototype termed subtilase cytotoxin (SubAB)[4]. In the case of SubAB, the A subunit (SubA) was found to be a subtilase family serine protease with exquisite specificity for the essential endoplasmic reticulum chaperone BiP/GRP78[5]. Structural studies revealed that unlike most subtilases, SubA possessed an unusually deep active site cleft, explaining its exquisite substrate specificity[5]. SubA has proven to be a powerful tool for examining the role of BiP in diverse cellular processes and it also has potential as a cancer therapeutic[6,7]. Significantly, glycan array analysis has shown that the B subunit of the toxin (SubB) has a high degree of binding specificity for glycans terminating with α2-3-linked N-glycolylneuraminic acid (Neu5Gc), a sialic acid that humans cannot synthesise[8]. Of all the glycans on the array, the best binding occurred with Neu5Gcα2-3Galβ1-4GlcNAcβ-. Binding of labelled toxin to the array was reduced 20-fold if the Neu5Gc was changed to Neu5Ac; over 30-fold if the Neu5Gc linkage was changed from α2-3 to α2-6; and 100-fold if the sialic acid was removed. The overall pattern of binding to structures represented on the array indicated that SubB has a high affinity for terminal α2-3-linked Neu5Gc with little discrimination for the penultimate moiety. The crystal structure of the SubB-Neu5Gc complex revealed the basis for this specificity. The additional hydroxyl on the methyl group of the N-acetyl moiety that distinguishes Neu5Gc from Neu5Ac interacts with Tyr78$^{OH}$ of SubB and hydrogen bonds with the main chain of Met10[8]. These key interactions could not occur with Neu5Ac, thus explaining the marked preference for Neu5Gc. Guided by the structural data, key residues were mutagenized in the predicted binding pocket, and this abrogated glycan recognition, cell binding and toxicity. SubB amino acids S12 and Y78 form crucial stabilizing bonds with Neu5Gc[8]. An S12A mutation abolished glycan binding completely, while a Y78F mutation that prevents interactions with the $C^{11}$ OH group that distinguishes Neu5Gc from Neu5Ac reduced glycan binding by 90% and abolished preference of the mutant SubB protein for Neu5Gc over Neu5Ac[8].

The most prominent form of aberrant glycosylation in human cancers is the expression of glycans terminated by Neu5Gc. Neu5Gc is not expressed in significant levels on normal healthy human cells[9-12] as humans cannot synthesise Neu5Gc due to an inactivating mutation in the CMAH gene[13]. Nevertheless, research suggests that Neu5Gc presentation in cancer patients can be explained by Neu5Gc absorption through dietary intake of red meat and dairy products, which are the richest sources of Neu5Gc[14]. The presence of Neu5Gc is prognostically important, because its expression frequently correlates with invasiveness, metastasis and the tumour grade[10]. Preferential display of Neu5Gc glycans on cancer cells may be at least partly explained by the hypoxic tumour environment, which markedly induces expression of the sialic acid transporter sialin, resulting in increased display of Neu5Gc and other sialic acids on the cell surface[15]. Due to the fact that sialyl-conjugates regulate adhesion and promote cell mobility, such alterations in surface sialylation may influence the colonisation and metastatic potential of tumour cells[16]. Elevated levels of abnormal sialic acids such as Neu5Gc have been observed in breast, ovarian, prostate, colon and lung cancer[11,12]. Importantly, incorporation of Neu5Gc in cancer cells is most prominent in soluble glycoproteins found both in the extracellular space and inside the cell, and Neu5Gc is the dominant sialic acid in glycoproteins secreted from cancer cells into the surrounding tissues[9]. The expression of Neu5Gc in cancer is also known to drive production of xenoautoantibodies against Neu5Gc[17,18]. These anti-Neu5Gc antibodies are being investigated to determine their potential for novel diagnostics, prognostics, and therapeutics in human carcinomas[17].

SUMMARY

The present invention is directed to a mutant subtilase cytotoxin B subunit protein (SubB) which can bind glycans having α2-3-linked N-glycolylneuraminic acid and glycans having α2-6-linked N-glycolylneuraminic acid. Thus, the mutant SubB protein has a previously undescribed ability to bind glycans having α2-6-linked N-glycolylneuraminic acid, while not losing the ability to bind glycans having α2-3-linked N-glycolylneuraminic acid. This provides a mutant SubB protein that can be used to detect and target a broader spectrum of N-glycolylneuraminic acid-containing glycans than was previously possible.

An aspect of the invention provides an isolated protein comprising an amino acid sequence of SubB wherein one or more amino acid residues of the amino acid sequence TTSTE (SEQ ID NO:3) are modified, wherein the isolated protein is capable of binding α2-3-linked N-glycolylneuraminic acid and α2-6-linked N-glycolylneuraminic acid.

In an embodiment, the one or more modified amino acid residues are underlined in the amino acid sequence TT<u>ST</u>E (SEQ ID NO:3)

In one embodiment, both of the underlined amino acids are deleted.

In one particular embodiment, the isolated protein comprises the amino acid sequence of SEQ ID NO:1.

In another particular embodiment, the isolated protein comprises a deletion of one or more of the amino acid residues are underlined in the amino acid sequence TTS<u>T</u>E (SEQ ID NO:3). Suitably, the isolated protein of this embodiment can bind Neu5Ac glycans such as Neu5Ac-α2-6-lac and Neu5Ac-α2-3-lac. In one embodiment, both of the underlined amino acids are deleted.

This aspect also provides variants, fragments and derivatives of the isolated protein.

Another aspect of the invention provides an isolated molecular complex comprising the isolated protein of the first aspect and a glycan comprising α2-3-linked N-glycolylneuraminic acid and/or α2-6-linked N-glycolylneuraminic acid.

Yet another aspect of the invention provides a composition comprising the isolated protein of the first aspect.

In one embodiment the composition is a pharmaceutical composition.

In another embodiment, the composition is a diagnostic composition.

Still yet another aspect of the invention provides a method of detecting α2-3-linked N-glycolylneuraminic acid and/or α2-6-linked N-glycolylneuraminic acid, said method including the step of combining the isolated protein of the first aspect with a sample to thereby form a detectable complex comprising the isolated protein of the first aspect and α2-3-linked N-glycolylneuraminic acid and/or α2-6-linked N-glycolylneuraminic acid.

In some embodiments, the α2-3-linked N-glycolylneuraminic acid and/or α2-6-linked N-glycolylneuraminic acid may be expressed by a tumour cell or feline blood cells.

In another embodiment, the α2-3-linked N-glycolylneuraminic acid and/or α2-6-linked N-glycolylneuraminic acid may be a contaminant in a sample or preparation comprising recombinant glycosylated drugs, antibodies and other therapeutic biomolecules for human administration.

Another aspect of the invention provides a method of isolating a glycan or a cell expressing the glycan, the glycan comprising α2-3-linked N-glycolylneuraminic acid and/or an α2-6-linked N-glycolylneuraminic acid, said method including the steps of: combining the isolated protein disclosed herein with a sample to thereby form a complex comprising the isolated protein and α2-3-linked N-glycolylneuraminic acid and/or α2-6-linked N-glycolylneuraminic acid; and isolating the protein or cell.

In some embodiments, the cell is a tumour cell or a feline blood cell.

In another embodiment, the α2-3-linked N-glycolylneuraminic acid and/or α2-6-linked N-glycolylneuraminic acid may be a contaminant in a preparation or formulation comprising recombinant glycosylated drugs, antibodies and other therapeutic biomolecules for human administration.

Another aspect of the invention provides a method of treating cancer in a subject, said method including the step of the isolated protein of the first aspect, or the composition of the aforementioned aspect, to the subject to thereby selectively target a cancer cell expressing an α2-3-linked N-glycolylneuraminic acid and/or α2-6-linked N-glycolylneuraminic acid.

Suitably, the isolated protein of the first aspect is coupled to a cytotoxic agent.

A further aspect of the invention provides an isolated nucleic acid encoding the isolated protein of the first aspect.

Another further aspect of the invention provides a genetic construct comprising the isolated nucleic acid of the second aspect.

Yet another further aspect of the invention provides a host cell comprising the genetic construct of the aforementioned aspect.

Still yet another further aspect of the invention provides an antibody or antibody fragment which binds or is raised against the isolated protein of the aforementioned aspect.

Suitably, the antibody or antibody fragment binds an epitope comprising one or more modified amino acid residues underlined in the amino acid sequence TTSTE (SEQ ID NO:3).

Related aspects of the invention provide kits comprising the isolated protein, isolated nucleic acid, composition, genetic construct and/or antibody, such as for use in detecting α2-3-linked N-glycolylneuraminic acid and/or α2-6-linked N-glycolylneuraminic acid or therapeutic targeting of tumour cells expressing α2-3-linked N-glycolylneuraminic acid and/or α2-6-linked N-glycolylneuraminic acid, although without limitation thereto.

Throughout this specification, unless otherwise indicated, "comprise", "comprises" and "comprising" are used inclusively rather than exclusively, so that a stated integer or group of integers may include one or more other non-stated integers or groups of integers.

By "consist essentially of" is meant in this context that the isolated protein or immunogenic fragment has one, two or no more than three amino acid residues in addition to the recited amino acid sequence. The additional amino acid residues may occur at the N- and/or C-termini of the recited amino acid sequence, although without limitation thereto.

It will also be appreciated that the indefinite articles "a" and "an" are not to be read as singular or as otherwise excluding more than one or more than a single subject to which the indefinite article refers. For example, "a" protein includes one protein, one or more proteins or a plurality of proteins.

BRIEF DESCRIPTION OF THE FIGURES

FIG. 5. NeuAc and NeuGc oxonium ions from human and bovine alpha-1-acid glycoprotein tryptic digests. Low mass region of MS/MS spectra of (A) glycopeptide ion at an m/z of 1183.163+ corresponding to peptide TFMLAASWN [Hex2FlexNAc2NeuAc1NeuGc1+Man3GlcNAc2]GTK (SEQ ID NO:9) from bovine alpha-1-acid glycoprotein and (B) glycopeptide ion at an m/z of 1122.284+ corresponding to peptide QDQCIYN[Hex3HexNAc3NeuAc2+ Man3GlcNAc2]TTYLNVQR (SEQ ID NO:10) from human alpha-1-acid glycoprotein showing abundant oxonium ions, including NeuAc-specific 274.1 and 292.1, and NeuGc-specific 290.1 and 308.1. (C) Intensity of NeuAc- and NeuGc-specific oxonium ions as a proportion of the total ion intensity from all MS/MS spectra from LC-MS/MS analysis of human and bovine alpha-1-acid glycoprotein tryptic digests. (D) Protein gel of the human and bovine AGP used in MS, ELISA, Biacore and dot blot.

DETAILED DESCRIPTION

Figure 1A:
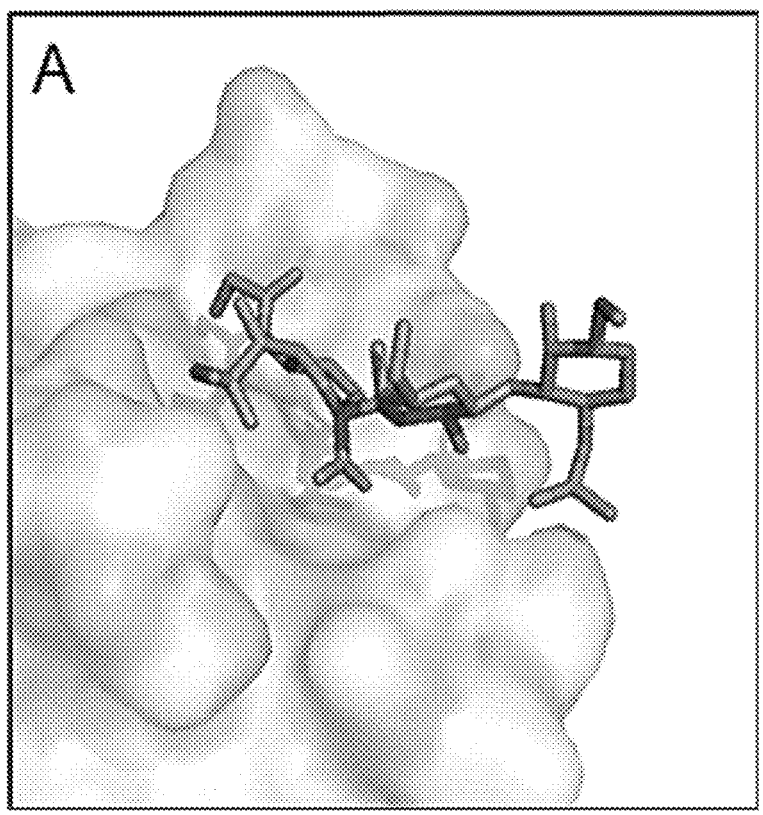
FIG. 1. Surface representation of SubB in complex with (A) Neu5Gcα2-3Galβ1-3GlcNAc (determined from a X-ray crystal structure (Byres et al., 2008)) and (B) Neu5Gcα2-6Galβ1-3Glc (modeled with the X-ray crystal structure). Trisaccharides are shown as a green or cyan stick with red and blue residues representing oxygen and nitrogen, respectively.

The present invention relates to an engineered mutant subtilase cytotoxin B subunit (SubB) protein that has one or more modified amino acid residues of the amino acid sequence TTSTE (SEQ ID NO:3) that can bind glycans terminating in either α2-3-linked or α2-6-linked Neu5Gc. The isolated protein may be used in methods for detecting glycans comprising α2-3-linked N-glycolylneuraminic acid and/or α2-6-linked N-glycolylneuraminic acid, such as expressed by certain tumour cells and also expressed by type A feline blood cells. Such glycans may also be contaminants in drug and other biomolecule preparations. Thus other aspects of the invention may relate to purifying, removing or depleting glycans comprising α2-3-linked N-glycolylneuraminic acid and/or α2-6-linked N-glycolylneuraminic acid, or cells that express these glycans. A further aspect of the invention relates to therapeutic uses of the isolated protein for targeted delivery of anti-cancer agents to certain tumour cells.

For the purposes of this invention, by "isolated" is meant material that has been removed from its natural state or otherwise been subjected to human manipulation. Isolated material may be partly, substantially or essentially free from, or depleted of, components that normally accompany it in its natural state. Isolated material may be in native, chemical synthetic or recombinant form. In some embodiments, isolated material may be in enriched, partially purified or purified form.

As used herein a "sample" may be any fraction, piece, portion or part that is representative of a larger entity. The sample may be of a pharmaceutical, drug, antibody or other therapeutic formulation or preparation or a biological sample such as obtained from a human, animal or other biological source. In some embodiments, a biological sample may be a cell or tissue sample such as a biopsy, smear, tissue section or cell pellet or a fluid sample such as comprising urine, serum, plasma, cerebrospinal fluid or saliva, although without limitation thereto.

As generally, used herein, a "composition" comprises an isolated protein, nucleic acid, genetic construct, antibody or other molecule together with one or more other components such as water or other solvents, salts, buffering agents and/or stabilizers, although without limitation thereto. In one particular embodiment, a "diagnostic" composition may comprise one or more other molecular components that facilitate detection of proteins that comprise α2-3-linked N-glycolylneuraminic acid and/or α2-6-linked N-glycolylneuraminic acid. Such components may include enzyme substrates, secondary antibodies, colour reagents, labels and catalysts (e.g "detection reagents") as will be described in more detail hereinafter. In other particular embodiments, a "pharmaceutical" composition may comprise one or more other molecular components that facilitate therapeutic administration of the isolated protein disclosed herein (e.g. a carrier, diluent or excipient), as will be described in more detail hereinafter.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

As generally used herein a "glycan" is a glycoprotein, glycolipid or other carbohydrate-containing macromolecule, and includes molecules that may be referred to as peptidoglycans, glycoproteins, glycopeptides, glycolipoproteins and the like. A particular glycan comprises N-glycolylneuraminic acid (Neu5Gc). The glycan may comprise α2-3-linked N-glycolylneuraminic acid or α2-6-linked N-glycolylneuraminic acid. Suitably, the α2-3-linked N-glycolylneuraminic acid and α2-6-linked N-glycolylneuraminic acids are terminal sialic acids. By way of example, α2-3-linked N-glycolylneuraminic acid is a terminal sialic acid such as in Neu5Gcα2-3Galβ1-4GlcNAcβ-; and α2-6-linked N-glycolylneuraminic acid is a terminal sialic acid in Neu5Gcα2-6Galβ1-3Glc-.

As will be appreciated from the foregoing, a preferred aspect of the invention provides an isolated protein comprising an amino acid sequence of SubB protein that has one or more modified amino acid residues of the amino acid sequence TTSTE, wherein the isolated protein is capable of binding a glycan comprising α2-3-linked N-glycolylneuraminic acid and a glycan comprising α2-6-linked N-glycolylneuraminic acid. A related aspect of the invention provides an isolated molecular complex comprising the isolated protein of the first aspect and a glycan comprising α2-3-linked N-glycolylneuraminic acid and/or α2-6-linked N-glycolylneuraminic acid.

In this context, by "capable of binding α2-3-linked N-glycolylneuraminic acid and α2-6-linked N-glycolylneuraminic acid" means that the isolated protein binds α2-6-linked N-glycolylneuraminic acid glycans with substantially greater affinity than does a wild-type SubB protein, while also binding α2-3-linked N-glycolylneuraminic acid glycans with a comparable affinity to that of a wild-type SubB protein. In a particular embodiment, the isolated protein binds α2-6-linked N-glycolylneuraminic acid glycans with an affinity of about 5-15 mM, about 7-12 nM or about 8-10 nM. In a particular embodiment, the isolated protein binds α2-3-linked N-glycolylneuraminic acid glycans with an affinity of about 8-20 nM, 10-18 mM or about 14-16 nM.

The amino acid sequence TTSTE (SEQ ID NO:3) is normally present in a wild-type SubB protein. Wild-type SubB protein may comprise an amino acid sequence set forth in SEQ ID NO:2:

```
  1 MTIKRFFVCA GIMGCLSLNP AMAEWTGDAR DGMFSGVVIT QFHTGQIDNK PYFCIEGKQS
 61 AGSSISACSM KNSSVWGASF STLYNQALYF YTTGQPVRIY YKPGVWTYPP FVKALTSNAL
121 VGLSTCTTST ECFGPDRKKN S
```

The underlined residues are an N-terminal region that is absent in the mature form of SubB. Numbering used herein therefore starts at glutamate residue 24 (i.e Glu24=residue 1). Using this numbering, the bolded residues TTSTE (SEQ ID NO:3) correspond to the "T104-E108 loop" (residues 127-131 of SEQ ID NO:2). It is proposed that the tertiary sugar of the α2-6 structure is folded back onto the SubB protein surface, making close contact with a loop comprising SubB residues T104-E108 (residues 127-131 of SEQ ID NO:2). This loop is stabilised by a disulphide bond between C103 and C109 (residues 126 and 132 of SEQ ID NO:2). The resultant steric hindrance distorts the docking of the terminal Neu5Gc into the binding pocket, accounting for the significantly poorer binding of α2-6-linked Neu5Gc structures observed on the original glycan array analysis of SubB[8]. Modification of one or more residues in the loop enhance binding of a mutant SubB protein to the α2-6 structure while also allowing binding to α2-3 structures. Generally, amino acid deletions or substitutions that reduce or lower the "height" of the loop may be advantageous for improved binding of α2-6-linked Neu5Gc structures. In this context "height" may be a function of the distance an amino acid R group projects or extends from the peptide backbone in 3D space (e.g. valine has greater height than leucine). Thus, in one embodiment deletion of one or more of the TTSTE (SEQ ID NO:3) residues of the loop is preferred (referred to herein as a "deletion mutant"). Preferably, these are underlined in TTSTE (SEQ ID NO:3). Based on the numbering of the mature SubB amino acid sequence in SEQ ID NO:2, residues S106 and/or T107 (residues 129 and 130 of SEQ ID NO:2) are deleted. In a particularly preferred embodiment, residues S106 and T107 (residues 129 and 130 of SEQ ID NO:2) are deleted.

Thus, one particular embodiment of a mutant SubB protein comprises the amino acid sequence of SEQ ID NO:1:

```
 1 EWTGDARDGM FSGVVITQFH TGQIDNKPYF CIEGKQSAGS SISACSMKNS SVWGASFSTL
61 YNQALYFYTT GQPVRIYYKP GVWTYPPFVK ALTSNALVGL STCTTECFGP DRKKNS
```

In another embodiment, the isolated protein comprises a deletion of the amino acid residues underlined in the amino acid sequence TTSTE (SEQ ID NO:3).

Based on the numbering of the mature SubB amino acid sequence in SEQ ID NO:2, residues T107 and E108 (residues 130 and 131 of SEQ ID NO:2) are deleted. As will be evident from the data shown in Table 1, the isolated protein "deletion mutant" lacking T107 and E108 (residues 130 and 131 of SEQ ID NO:2) binds α2-6-linked N-glycolylneuraminic acid glycans with substantially greater affinity than does a wild-type SubB protein, while also binding α2-3-linked N-glycolylneuraminic acid glycans. However, in contrast to an S106 and T107 (residues 129 and 130 of SEQ ID NO:2) deletion mutant (such as in SEQ ID NO:1), the T107 and E108 (residues 130 and 131 of SEQ ID NO:2) deletion mutant can broadly bind glycans including Neu5Ac glycans such as Neu5Ac-α2-6-lac and Neu5Ac-β2-3-lac (e.g. see Table 1). It is also noted that WT SubB does not detectably bind Neu5Ac-α2-6-lac. Thus, the T107 and E108 (residues 130 and 131 of SEQ ID NO:2) deletion mutant protein may be a useful protein for binding or detecting Neu5Gc glycans such as α2-6-linked N-glycolylneuraminic acid glycans and α2-3-linked N-glycolylneuraminic acid glycans and also Neu5Ac glycans such as Neu5Ac-α2-6-lac and Neu5Ac-α2-3-lac.

Also provided are variants, fragments and derivatives of the isolated protein disclosed herein. Suitably, variants, fragments and derivatives of the isolated protein retain an ability to bind glycans terminating in α2-3-linked and α2-6-linked Neu5Gc. In particular embodiments, this is at least 50%, 55%, 60%, 65%, 70%, 75%, 80%, 85%, 90%, 91%, 92%, 93%, 94%, 95%, 96%, 97%, 98% or 99% of the ability of the isolated protein of an isolated protein disclosed herein to bind glycans terminating in α2-3-linked and α2-6-linked Neu5Gc.

As used herein, a peptide "variant" has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with an amino acid sequence of an isolated protein disclosed herein. The peptide "variant" disclosed herein may have one or more amino acids deleted or substituted by different amino acids. It is well understood in the art that some amino acids may be substituted or deleted without changing biological activity of the peptide (conservative substitutions).

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e. resulting in the highest percentage homology over the comparison window) generated by any of the various methods selected.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Reference is also made to the BLAST family of algorithms which uses the method of Altschul et al. (1990) *J. Mol. Biol.* 215: 405-410), the psi-Blast algorithm (Nucl. Acids Res. (1997) 25 3389-3402), FASTA (which uses the method of Pearson and Lipman (1988) *PNAS USA* 85: 2444-2448), the Smith-Waterman algorithm (Smith and Waterman (1981) *J. Mol Biol.* 147: 195-197), or the TBLASTN program, of Altschul et al. (1990) supra, generally employing default parameters.

A detailed discussion of sequence analysis can be found in Unit 19.3 of CURRENT PROTOCOLS IN MOLECULAR BIOLOGY Eds. Ausubel et al. (John Wiley & Sons Inc NY, 1995-2015).

Sequence comparison may be made over the full-length of the relevant sequence described herein.

The tem' "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

The invention also provides fragments of the isolated peptide disclosed herein. In some embodiments, fragments may comprise, consist essentially of, or consist of 10, 15, 20, 25, 30, 35, 40, 45, 50, 55, 60, 65, 70, 75, 80, 85, 90, 95, 100, 105, 110, 115 contiguous amino acids of an isolated protein disclosed herein.

Derivatives of the isolated peptide disclosed herein are also provided.

As used herein, "derivative" proteins or peptides have been altered, for example by conjugation or complexing with other chemical moieties, by post-translational modification (e.g. phosphorylation, ubiquitination, glycosylation), chemical modification (e.g. cross-linking, acetylation, biotinylation, oxidation or reduction and the like), conjugation with labels (e.g. fluorophores, enzymes, radioactive isotopes) and/or inclusion of additional amino acid sequences as would be understood in the art.

In this regard, the skilled person is referred to Chapter 15 of CURRENT PROTOCOLS IN PROTEIN SCIENCE, Eds. Coligan et al. (John Wiley & Sons NY 1995-2015) for more extensive methodology relating to chemical modification of proteins.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. polyhistidine) fusion partners, maltose binding protein (MBP), Protein A, glutathione S-transferase (GST), fluorescent protein sequences (e.g. GFP), epitope tags such as myc, FLAG and haemagglutinin tags.

The isolated peptides, variant and/or derivatives of the present invention may be produced by any means known in the art, including but not limited to, chemical synthesis and recombinant DNA technology.

Chemical synthesis is inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2014). In this regard, reference is also made to International Publication WO 99/02550 and International Publication WO 97/45444.

Recombinant proteins may be conveniently prepared by a person skilled in the art using standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. NY USA 1995-2014), in particular Chapters 10 and 16; and CURRENT PROTOCOLS IN PROTEIN SCIENCE Eds. Coligan et al., (John Wiley & Sons, Inc. NY USA 1995-2014), in particular Chapters 1, 5 and 6.

Particular embodiments of "derivatives" of the isolated protein that may be useful in detection, purification and/or therapeutic methods are described as follows.

An aspect of the invention provides a method of detecting α2-3-linked N-glycolylneuraminic acid and/or α2-6-linked N-glycolylneuraminic acid, said method including the step of combining the isolated protein disclosed herein with a sample to thereby form a detectable complex comprising the isolated protein of the first aspect and α2-3-linked N-glycolylneuraminic acid and/or α2-6-linked N-glycolylneuraminic acid.

α2-3-linked N-glycolylneuraminic acid and/or α2-6-linked N-glycolylneuraminic acid may be components of glycans expressed by tumour cells, and certain blood cells such as feline blood cells. In particular embodiments, glycans comprising α2-3-linked N-glycolylneuraminic acid and/or α2-6-linked N-glycolylneuraminic acid may be expressed by human carcinomas, with elevated expression detected in breast, ovarian, prostate, colon and lung cancer. In other particular embodiments, N-glycolylneuraminic acid defines the "A" blood group of felines while N-acetylneuraminic acid defines the "B" blood group of felines.

Accordingly, the isolated protein may be used for detecting the presence of α2-3-linked N-glycolylneuraminic acid and/or α2-6-linked N-glycolylneuraminic acid-expressing tumour cells in a patient sample, such as a biopsy, fluid sample, smear or the like. In another embodiment, the isolated protein may be used for feline blood-typing by detecting blood cells that express N-glycolylneuraminic acid glycans, such as comprising α2-3-linked N-glycolylneuraminic acid and/or α2-6-linked N-glycolylneuraminic acid, in a feline blood sample.

In other particular embodiments glycans comprising α2-3-linked N-glycolylneuraminic acid and/or α2-6-linked N-glycolylneuraminic acid may be present in a preparation or formulation comprising drugs, antibodies or other therapeutic biomolecules for human administration.

Recombinant glycosylated drugs, antibodies and other therapeutic biomolecules for human administration are often produced in non-human mammalian cell lines which can synthesize and/or metabolically incorporate the non-human sialic acid N-glycolylneuraminic acid (Neu5Gc). Some humans have high levels of circulating anti-Neu5Gc antibodies. By way of example, the clinically effective anti-EGFR mAb Cetuximab may have covalently-bound Neu5Gc. Anti-Neu5Gc antibodies from normal humans interact with Cetuximab in a Neu5Gc-specific manner and generate immune complexes in vitro. These antibodies may enhance Cetuximab (or other therapeutic antibody) clearance in vivo. Thus Neu5Gc contamination of drugs, antibodies and other therapeutic biomolecules may adversely affect half-life, efficacy and immune reactions in patients administered such drugs. While it may be possible to avoid Neu5Gc contamination by using Neu5Gc-deficient cells and media, this may not be an optimal solution in all cases. Thus, certain embodiments of the invention provide detection of α2-3-linked N-glycolylneuraminic acid and/or α2-6-linked N-glycolylneuraminic acid in drugs, antibodies or other therapeutic biomolecules for human administration. Other embodiments of the invention provide isolation, depletion or removal of α2-3-linked N-glycolylneuraminic acid and/or α2-6-linked N-glycolylneuraminic acid-containing contaminants from drugs, antibodies or other therapeutic biomolecules for human administration.

Accordingly, it may be advantageous to couple, bind, affix or otherwise link the isolated protein (e.g. of an isolated protein disclosed herein such as comprising the amino acid sequence of SEQ ID NO:1), or a fragment or variant thereof, to an agent that facilitates detection of α2-3-linked N-glycolylneuraminic acid and/or α2-6-linked N-glycolylneuraminic acid. In a preferred form, the isolated protein is covalently coupled to a label.

In other embodiments, a labelled secondary binding agent such as an antibody or antibody fragment may be used to detect the isolated protein when bound to glycans comprising α2-3-linked N-glycolylneuraminic acid and/or α2-6-linked N-glycolylneuraminic acid.

According to either of the above embodiments, a label may be selected from a group including a chromogen, a catalyst, biotin, avidin, digoxigenin, an enzyme, a fluorophore, a chemiluminescent molecule or a radioisotope although without limitation thereto.

The fluorophore may be, for example, fluorescein isothiocyanate (FITC), Alexa dyes, tetramethylrhodamine isothiocyanate (TRITL), allophycocyanin (APC), Texas Red, FAM, ROX, Cy5, Cy3, or R-Phycoeiythrin (RPE) although without limitation thereto.

The enzyme may be horseradish peroxidase (HRP), alkaline phosphatase (AP), β-galactosidase or glucose oxidase, although without limitation thereto. Appropriate substrates include diaminobanzidine (DAB), permanent red, 3-ethylbenzthiazoline sulfonic acid (ABTS), 5-bromo-4-chloro-3-indolyl phosphate (BCIP), nitro blue tetrazolium (NBT), 3,3',5,5'-tetramethyl benzidine (TNB) and 4-chloro-1-naphthol (4-CN), although without limitation thereto. A non-limiting example of a chemiluminescent substrate is Luminol™, which is oxidized in the presence of HRP and hydrogen peroxide to form an excited state product (3-aminophthalate).

Radioisotope labels may include $^{125}$I, $^{131}$I, $^{51}$Cr and $^{99}$Tc, although without limitation thereto.

In the case of a direct visual label, use may be made of a colloidal metallic or non-metallic particle, a dye particle, an organic polymer, a latex particle, a liposome, a minicell or other vesicle containing a signal producing substance and the like.

The labeled isolated protein may be used in detection systems such as histochemistry, flow cytometry, fluorescence microscopy and ELISAs, body imaging (e.g PET scans) and nuclear medicine although without limitation thereto.

In a further aspect, the invention provides a method of isolating a glycan or a cell expressing the glycan, the glycan comprising α2-3-linked N-glycolylneuraminic acid and/or an α2-6-linked N-glycolylneuraminic acid, said method including the steps of: combining the isolated protein disclosed herein with a sample to thereby form a complex comprising the isolated protein and α2-3-linked N-glycolylneuraminic acid and/or α2-6-linked N-glycolylneuraminic acid; and isolating the glycan or the cell. In this context, the term "isolating" preferably refers to purifying, enriching or depleting or removing the glycan comprising α2-3-linked N-glycolylneuraminic acid and/or an α2-6-linked N-glycolylneuraminic acid, or cells expressing same.

In some embodiments, the isolated protein (e.g. comprising the amino acid sequence of SEQ ID NO:1), or a fragment or variant thereof, is coupled to a label as hereinbefore described, which facilitates detection of the glycan comprising α2-3-linked N-glycolylneuraminic acid and/or an α2-6-linked N-glycolylneuraminic acid, or cells expressing same. A non-limiting example includes a fluorescent label (such as hereinbefore described) which facilitates flow cytometric sorting of tumour cells or feline blood cells.

In another embodiment, the isolated protein disclosed herein, or a fragment or variant thereof, may be coupled, bound, affixed or otherwise linked to a substrate that facilitates isolation, enrichment, purification, depletion or removal of a glycan comprising α2-3-linked N-glycolylneuraminic acid and/or α2-6-linked N-glycolylneuraminic acid, or cells expressing same.

The isolated protein disclosed herein, or a fragment or variant thereof, may be coupled, bound, affixed or otherwise linked to a substrate that may be a bead, matrix, cross-linked polymer, gel, particle, surface or other solid or semi-solid substrate. In particular embodiments the substrate may be or comprise sepharose, agarose, Protein A, Protein G, a magnetic bead, a paramagnetic particle, or sensor chip surface (e.g. for BIACore or surface plasmon resonance). Suitably, a sample comprises a mixture of molecules that may comprise, or be suspected of comprising, α2-3-linked N-glycolylneuraminic acid and/or α2-6-linked N-glycolylneuraminic acid, or cells expressing same.

In certain embodiments, the isolated protein disclosed herein or a fragment or variant thereof, coupled, bound, affixed or otherwise linked to a substrate may be suitable for chromatography (e.g affinity chromatography), magnetic bead depletion or other techniques that facilitate isolation, enrichment, purification, depletion or removal of a glycan comprising α2-3-linked N-glycolylneuraminic acid and/or α2-6-linked N-glycolylneuraminic acid, or cells expressing same.

In a particular embodiment, the α2-3-linked N-glycolylneuraminic acid and/or an α2-6-linked N-glycolylneuraminic acid may be present as contaminants in a sample, whereby the complex formed between the isolated protein and α2-3-linked N-glycolylneuraminic acid and/or α2-6-linked N-glycolylneuraminic acid removes the contaminants from the sample. A particular example is a preparation or formulation comprising recombinant glycosylated drugs, antibodies and other therapeutic biomolecules for human administration, as hereinbefore described.

The isolated protein disclosed herein, such as comprising the amino acid sequence of SEQ ID NO:1, or a fragment, variant or derivative may be suitable for targeted delivery of anti-cancer compounds to tumour cells that express glycans comprising α2-3-linked N-glycolylneuraminic acid and/or α2-6-linked N-glycolylneuraminic acid. The ability to bind both α2-3-linked N-glycolylneuraminic acid and/or α2-6-linked N-glycolylneuraminic acid means that the present invention provides a far more efficacious targeted delivery system than could be provided using a wild-type SubB protein.

Accordingly, a further aspect of the invention provides a method of treating cancer in a subject, said method including the step of administering the isolated protein, or the composition disclosed herein, to the subject to thereby selectively target a cancer cell expressing an α2-3-linked N-glycolylneuraminic acid and/or α2-6-linked N-glycolylneuraminic acid.

As hereinbefore described, some tumour cells express glycans comprising α2-3-linked N-glycolylneuraminic acid and/or α2-6-linked N-glycolylneuraminic acid, whereas normal cells typically do not express these sugars. In particular embodiments, glycans comprising α2-3-linked N-glycolylneuraminic acid and/or α2-6-linked N-glycolylneuraminic acid may be expressed by human carcinomas, with elevated expression detected in breast, ovarian, prostate, colon and lung cancer, although without limitation thereto.

In an embodiment, the isolated protein may be coupled, bound, affixed or otherwise linked to a cytotoxic agent that facilitates binding to, and killing or disabling of, tumour cells that express α2-3-linked N-glycolylneuraminic acid and/or α2-6-linked N-glycolylneuraminic acid.

The cytotoxic agent may be a radionuclide, a chemotherapeutic drug, a mutagen, a toxin, a mitosis inhibitor or other anti-proliferative agent, a pro-apoptotic agent, a DNA intercalating agent or any other agent that assists or causes killing or disabling of tumour cells.

Non-limiting examples of radionuclides include $^{211}$At, $^{212}$Bl, $^{213}$Bi, $^{125}$I, $^{111}$In, $^{90}$Yt, $^{193}$Pt, $^{177}$Lu, $^{134}$Eu and $^{67}$Ga, although without limitation thereto.

Chemotherapeutic drugs, mutagens, toxins, mitosis inhibitors, pro-apoptotic agents and DNA intercalating agents may include doxorubicin, N-acetyl-γ-calicheamicin, maytansinoids, taxoids, auristatins and duocarmycins, although without limitation thereto. Chemotherapeutic drugs, mutagens, toxins, mitosis inhibitors, pro-apoptotic agents and DNA intercalating agents may be coupled to the isolated protein by a cleavable or non-cleavable linker to form a cleavable conjugate. Typically, the cleavable conjugate is internalized by the tumour cell where the cleavable linker is cleaved to release the drug into the cell. In the case of non-cleavable linkers, these may be preferred where it is essential that the drug is entirely localized to the targeted tumour cell and there is no "leakage" of the drug from the targeted tumour cell into adjacent cells, tissues or fluids. In some embodiments, the chemotherapeutic drugs, mutagens, toxins, mitosis inhibitors, pro-apoptotic and DNA intercalating agents may be in the form of a pro-drug which is activated upon internalization inside a targeted tumour cell.

In embodiments relating to therapeutic uses, the isolated protein (e.g. comprising the amino acid sequence of SEQ ID NO:1), or a fragment or variant thereof, may be administered as a pharmaceutical composition.

Suitably, the pharmaceutical composition comprises a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, liposomes and other lipid-based carriers, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991), which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunotherapeutic compositions, proteinaceous vaccines and nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Another aspect of the invention provides an antibody or antibody fragment that binds the isolated protein disclosed herein. Suitably, the antibody or antibody fragment does not bind a wild-type SubB protein (such as comprising the amino acid sequence of SEQ ID NO:2), or binds with at least 5 or 10-fold lower affinity compared to the affinity with which it binds the isolated protein disclosed herein (such as comprising the amino acid sequence of SEQ ID NO:1). Suitably, the antibody or antibody fragment binds an epitope of SEQ ID NO:1 comprising the one or more modified amino acid residues of the amino acid sequence TTSTE (SEQ ID NO:3).

As used herein an "antibody" is or comprises an immunoglobulin. The term "immunoglobulin" includes any antigen-binding protein product of a mammalian immunoglobulin gene complex, including immunoglobulin isotypes IgA, IgD, IgM, IgG and IgE and antigen-binding fragments thereof. Included in the term "immunoglobulin" are immunoglobulins that are chimeric or humanised or otherwise comprise altered or variant amino acid residues, sequences and/or glycosylation, whether naturally occurring or produced by human intervention (e.g. by recombinant DNA technology).

Antibody fragments include Fab and Fab'2 fragments, diabodies and single chain antibody fragments (e.g. scVs), although without limitation thereto. Typically, an antibody comprises respective light chain and heavy chain variable regions that each comprise CDR 1, 2 and 3 amino acid sequences The antibody or antibody fragment may comprise at least a portion of a CDR1, 2 and/or 3 amino acid sequence A preferred antibody fragment comprises at least one entire light chain variable region CDR and/or at least one entire heavy chain variable region CDR.

Antibodies and antibody fragments may be polyclonal or preferably monoclonal. Monoclonal antibodies may be produced using the standard method as for example, described in an article by Köhler & Milstein, 1975, Nature 256, 495, or by more recent modifications thereof as for example described in Chapter 2 of Coligan et al., CURRENT PROTOCOLS IN IMMUNOLOGY, by immortalizing spleen or other antibody producing cells derived from a production species which has been inoculated the isolated protein (e.g. comprising the amino acid sequence of SEQ ID NO:1) or a fragment or variant thereof. It will also be appreciated that antibodies may be produced as recombinant synthetic antibodies or antibody fragments by expressing a nucleic acid encoding the antibody or antibody fragment in an appropriate host cell. Recombinant synthetic antibody or antibody fragment heavy and light chains may be co-expressed from different expression vectors in the same host cell or expressed as a single chain antibody in a host cell. Non-limiting examples of recombinant antibody expression and selection techniques are provided in Chapter 17 of Coligan et al., CURRENT PROTOCOLS IN IMMUNOLOGY supra and Zuberbuhler et al., 2009, Protein Engineering, Design & Selection 22 169.

Antibodies and antibody fragments may be modified so as to be administrable to one species having been produced in, or originating from, another species without eliciting a deleterious immune response to the "foreign" antibody. In the context of humans, this is "humanization" of the antibody produced in, or originating from, another species. Such methods are well known in the art and generally involve recombinant "grafting" of non-human antibody complementarity determining regions (CDRs) onto a human antibody scaffold or backbone.

In some embodiments, the antibody or antibody fragment is labeled. Labels may be as hereinbefore described.

The invention also provides an isolated nucleic acid encoding the isolated protein disclosed herein, or a fragment or variant thereof. In an embodiment, the isolated nucleic acid encodes the isolated protein comprising the amino acid sequence set forth in SEQ ID NO:1, or a fragment or variant thereof.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

Also contemplated are variants of the isolated nucleic acid.

In an embodiment, a nucleic acid variant may have at least 70%, 75%, 80%, 85%, 90%, 91%, 92%, 93%, 94%, 95%, 96%, 97%, 98% or 99% nucleotide sequence identity to a nucleotide sequence encoding SEQ ID NO:1.

In another embodiment, a nucleic acid variant may hybridize to a nucleotide sequence encoding SEQ ID NO:1 under high stringency conditions.

High stringency conditions are well known in the art, such as described in Chapters 2.9 and 2.10 of Ausubel et al. CURRENT PROTOCOLS IN MOLECULAR BIOLOGY (John Wiley & Sons NY, 1995-2015) and in particular at pages 2.9.1 through 2.9.20.

Generally, stringency is dependent upon the concentration of one or more factors during hybridization and/or washing. Such factors may include ionic strength, detergent type and/or concentration, temperature, time, denaturant type and/or concentration, as are well understood in the art.

Specific, non-limiting examples of high stringency conditions include:—

(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;

(ii) 1% BSA, 1 mM EDTA, 0.5 M $NaHPO_4$ (pH 7.2), 7% SDS for hybridization at 65° C., and (a) 0.1×SSC, 0.1%

SDS; or (b) 0.5% BSA, 1 mM EDTA, 40 mM NaHPO$_4$ (pH 7.2), 1% SDS for washing at a temperature in excess of 65° C. for about one hour; and (iii) 0.2×SSC, 0.1% SDS for washing at or above 68° C. for about 20 minutes.

In general, washing is carried out at $T_m$=69.3+0.41 (G+C) %−12° C. In general, the $T_m$ of a duplex DNA decreases by about 1° C. with every increase of 1% in the number of mismatched bases.

In one aspect, the isolated nucleic acid is in a genetic construct that comprises the isolated nucleic acid operably linked or connected to one or more other genetic components. A genetic construct may be suitable for therapeutic delivery of the isolated nucleic acid or for recombinant protein production in a host cell.

Broadly, the genetic construct is in the form of, or comprises genetic components of, a plasmid, bacteriophage, a cosmid, a yeast or bacterial artificial chromosome as are well understood in the art. Genetic constructs may be suitable for maintenance and propagation of the isolated nucleic acid in bacteria or other host cells, for manipulation by recombinant DNA technology and/or expression of the nucleic acid or an encoded protein of the invention.

For the purposes of host cell expression, the genetic construct is an expression construct. Suitably, the expression construct comprises the nucleic acid of the invention operably linked to one or more additional sequences in an expression vector. An "expression vector" may be either a self-replicating extra-chromosomal vector such as a plasmid, or a vector that integrates into a host genome.

By "operably linked" is meant that said additional nucleotide sequence(s) is/are positioned relative to the nucleic acid of the invention preferably to initiate, regulate or otherwise control transcription.

Regulatory nucleotide sequences will generally be appropriate for the host cell used for expression. Numerous types of appropriate expression vectors and suitable regulatory sequences are known in the an for a variety of host cells.

Typically, said one or more regulatory nucleotide sequences may include, but are not limited to, promoter sequences, leader or signal sequences, ribosomal binding sites, polyadenylatioin sequences, transcriptional start and termination sequences, translational start and termination sequences, and enhancer or activator sequences.

Constitutive, repressible or inducible promoters as known in the art are contemplated by the invention.

The expression construct may also include an additional nucleotide sequence encoding a fusion partner (typically provided by the expression vector) so that the recombinant protein is expressed as a fusion protein, as hereinbefore described.

The expression construct may also include an additional nucleotide sequence encoding a selection marker such as amp$^R$, neo$^R$ or kan$^R$, although without limitation thereto.

In particular embodiments relating to delivery of isolated nucleic acids to a wound or to a subject, the expression construct may be in the form of plasmid DNA, suitably comprising a promoter operable in an animal cell (e.g. a CMV, an α A-crystallin or SV40 promoter). In other embodiments, the nucleic acid may be in the form of a viral construct such as an adenoviral, vaccinia, lentiviral or adeno-associated viral vector.

In a further aspect, the invention provides a host cell transformed with a nucleic acid molecule or a genetic construct described herein.

Suitable host cells for expression may be prokaryotic or eukaryotic. For example, suitable host cells may include but are not limited to mammalian cells (e.g. HeLa, Cos, NIH-3T3, HEK293T, Jurkat cells), yeast cells (e.g. *Saccharomyces cerevisiae*), insect cells (e.g. Sf9, *Trichoplusia ni*) utilized with or without a baculovirus expression system, plant cells (e.g. *Chlamydomonas reinhardtii, Phaeodactylum tricornutum*) or bacterial cells, such as *E. coli*. Introduction of genetic constructs into host cells (whether prokaryotic or eukaryotic) is well known in the art, as for example described in CURRENT PROTOCOLS IN MOLECULAR BIOLOGY Eds. Ausubel et al., (John Wiley & Sons, Inc. 1995-2015), in particular Chapters 9 and 16.

Related aspects of the invention provide kits comprising the isolated protein, isolated nucleic acid, genetic construct and/or antibody, such as for expression of the isolated protein, use in detecting α2-3-linked N-glycolylneuraminic acid and/or α2-6-linked N-glycolylneuraminic acid or therapeutic targeting of tumour cells expressing α2-3-linked N-glycolylneuraminic acid and/or α2-6-linked N-glycolylneuraminic acid, although without limitation thereto.

By way of example, kits for detecting α2-3-linked N-glycolylneuraminic acid and/or α2-6-linked N-glycolylneuraminic acid may comprise the isolated protein, which may be labeled or unlabeled, optionally a labeled secondary binding agent such as an antibody which binds the isolated protein, optionally one or more substrates for enzymes such as AP or HRP and instructions for use.

In another example, kits for expression of the isolated protein may comprise a genetic construct encoding the isolated protein, suitable host cells for transfection and expression of the isolated protein and instructions for use.

So that the invention may be readily understood and put into practical effect, reference is made to the following non-limiting Examples.

Examples

Introduction

Due to its known involvement in cancer and its normally low level in non-cancerous human tissues, detection of a large amount of Neu5Gc in serum and in tissues would be considered abnormal and would be indicative of the presence of a tumour. This raises the possibility of exploiting the specificity of SubB for Neu5Gc to develop a high-throughput diagnostic screening test for a range of cancers. However, the poor affinity for α2-6-linked Neu5Gc might impact on the sensitivity of such a test. In the present study, we have examined the interaction between SubB and glycans terminating in either α2-3-linked, or α2-6-linked, Neu5Gc, with a view to designing a SubB mutant with capacity to recognise both types of structures with high affinity.

Results

Structure-Guided Mutation of the Glycan Binding Site of SubB

Figure 1B:
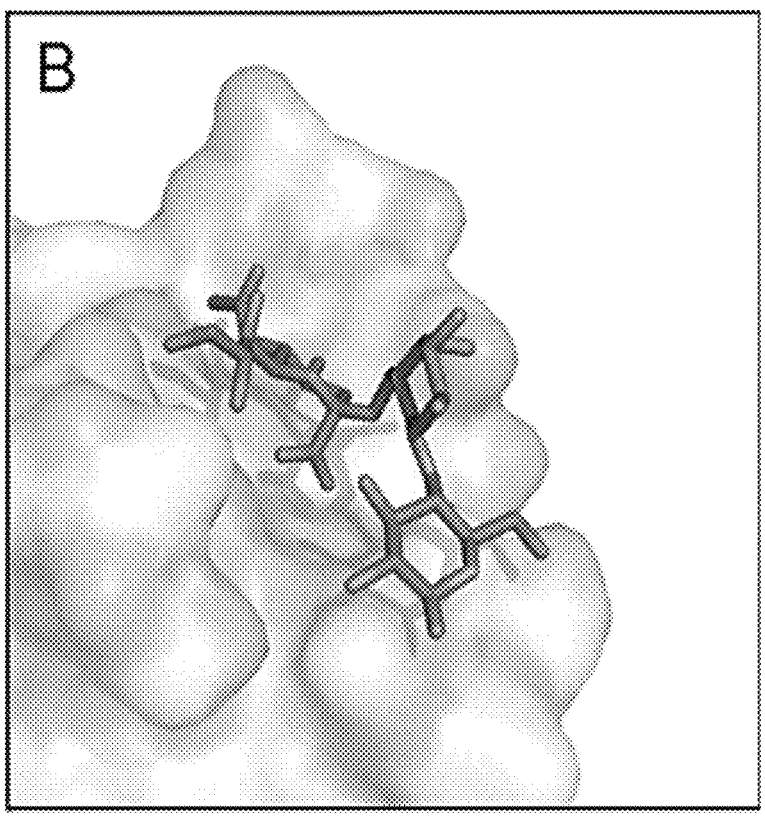

In order to understand the molecular basis for the preference for α2-3-linked structures, we have compared the interaction between SubB and Neu5Gcα2-3Galβ1-3GlcNAc (determined by X-ray crystallography) vs Neu5Gcα2-6Galβ1-3Glc (FIG. 1). Whereas the sub-terminal sugars of the former glycan extend freely out into the solvent, as reported previously[8], the tertiary sugar of the α2-6 structure is folded back onto the SubB surface, making close contact with a loop comprising SubB residues T104-E108 (residues 127-131 of SEQ ID NO:2). This loop is stabilised by a disulphide bond between C103 and C109 (residues 126 and 132 of SEQ ID NO:2). The resultant steric hindrance distorts the docking of the terminal Neu5Gc into the binding pocket, accounting for the significantly poorer binding of α2-6-linked Neu5Gc structures observed on the original glycan array analysis.

Figure 2:
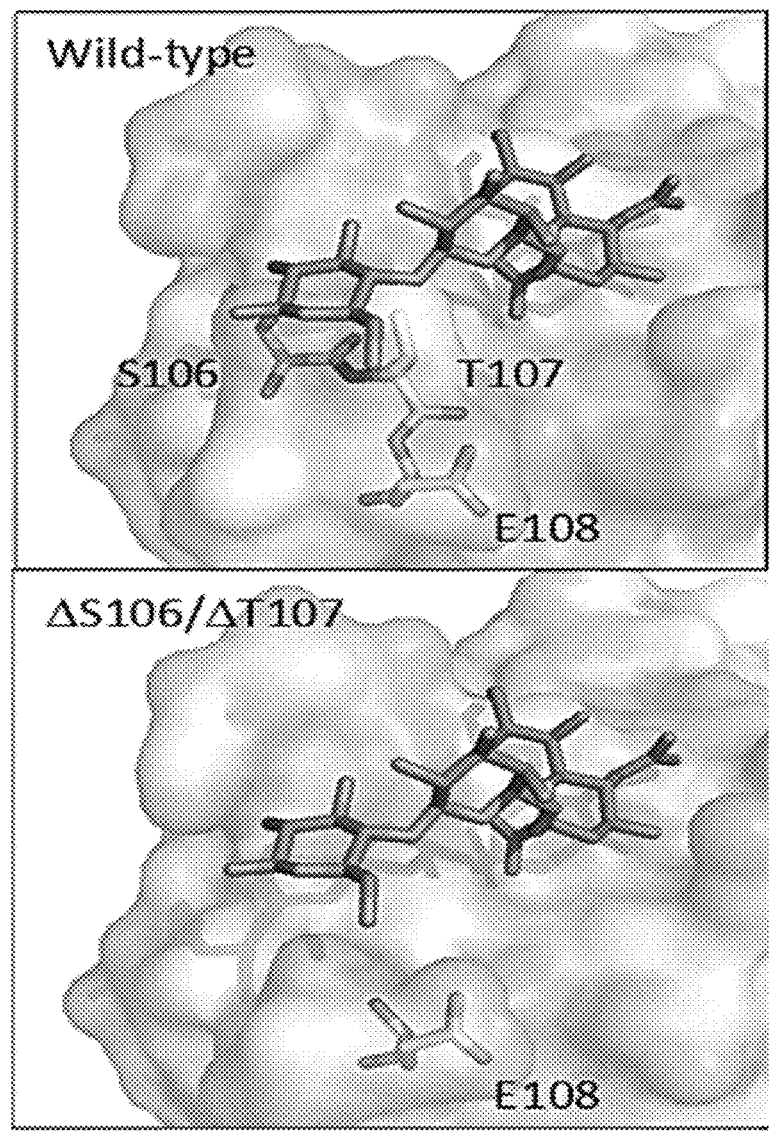
FIG. 2. Surface representation of the wild-type and SubB mutants modeled with Neu5Gcα2-6Galβ1-3Glc (shown as a cyan stick). The imitated SubB residues are shown as grey sticks and red and blue residues represent oxygen and nitrogen, respectively.
Figure 2:
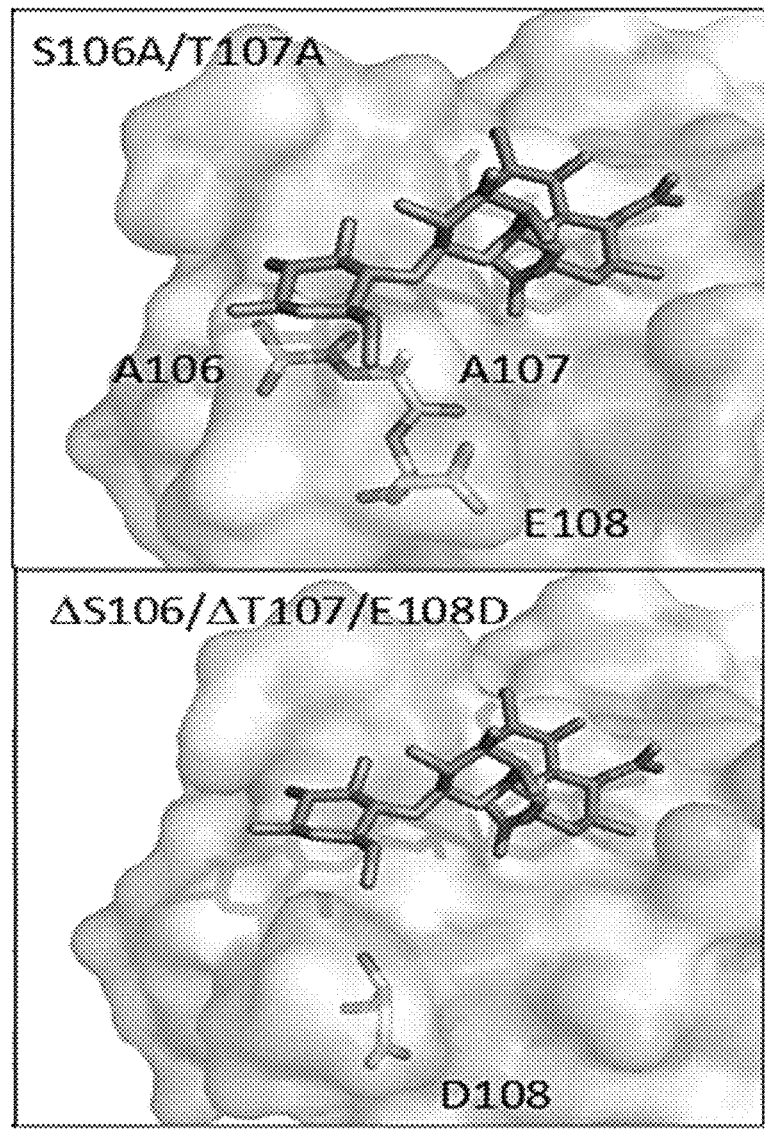

Since α2-6-linked sialic acids are common markers of colon cancer[19,20] and are linked to prognosis in a range of cancers[21], we used molecular engineering to improve binding of α2-6-linked Neu5Gc structures to SubB by designing a series of substitution and/or deletion mutants to reduce the height of the T104-E108 loop (residues 127-131 of SEQ ID NO:2). We have modelled the interactions between these SubB mutants and Neu5Gcα2-6Galβ1-3Glc and predict that they would have improved recognition of α2-6-linked Neu5Gc without significantly impacting on α2-3-linked Neu5Gc binding, as shown in FIG. 2. We then constructed recombinant subB genes and expressed and purified the various proteins as C terminal His$_6$-tagged fusion proteins from recombinant E. coli (see Methods). SubB proteins with single or double amino acid substitutions (T107A (residue 130 of SEQ ID NO:2) and S106A/T107A (residues 129-130 of SEQ ID NO:2)), a double deletion mutant (ΔS106/ΔT107 (residues 129-130 of SEQ ID NO:2)) and a triple mutant (ΔS106/ΔT107/E108D (residues 129-131 of SEQ ID NO:2)) were successfully purified.

Surface Plasmon Resonance of Engineered SubB Mutants

Purified SubB and the various mutant derivatives were then immobilized on Biacore chips and tested for binding affinities to a range of Neu5Ac- or Neu5Gc-terminating structures (free sialic acid, sialic acid-α2-3-lactose and sialic acid-α2-6-lactose), as well as to human and bovine al-acid glycoprotein (AGP), by surface plasmon resonance (SPR) (Table 1). The human AGP glycans contain Neu5Ac[22,23] and the bovine AGP glycans contain both Neu5Ac and Neu5Gc[23]. The MS glycoproteomic analysis (FIG. 5) was performed to confirm the Neu5Ac and Neu5Gc distribution in the human and bovine AGP used in the SPR study. Wild-type SubB was found to have high affinity for α2-3-linked Neu5Gc-lactose and free Neu5Gc, as predicted from the glycan array result, with nanomolar binding affinities observed. No binding was observed for the α2-6-linked Neu5Gc-lactose (tested to a maximum concentration of 25 μM) and 2.2 μM affinity was observed for α2-3-linked Neu5Ac—a more than 300-fold decrease in binding compared to the equivalent Neu5Gc structure. The wild-type SubB also had a 13-fold reduced binding affinity for human AGP compared to bovine AGP. The mutation in SubB$_{T107A}$ had no significant effect on binding to any of the tested structures compared to the wild-type protein. SubB$_{S106A/T107A}$ had improved binding to α2-6-linked structures, but this improvement was seen for both Neu5Ac and Neu5Gc. The nanomolar range affinities observed for all linked sugars tested reveals that SubB$_{S106A/T107A}$ is a good all-round sialic acid-recognising lectin. The SubB$_{ΔS106/ΔT107/E108D}$ mutant had improved recognition of α2-6-linked Neu5Gc without changing the binding to the α2-6-linked Neu5Ac structures. However, the difference in affinity between α2-3-linked Neu5Ac and α2-3-linked Neu5Gc was reduced to 50-fold compared to the 300-fold observed for the wild-type. The SubB$_{ΔS106/ΔT107}$ mutant was significantly improved for Neu5Gc vs Neu5Ac discrimination compared to the wild-type protein, and had the ability to bind α2-3-linked Neu5Gc and α2-6-linked Neu5Gc with binding affinities that were not significantly different between the two structures (15.3 nM vs 8.5 nM, respectively; P=0.12). Thus, SubB$_{ΔS106/ΔT107}$ exhibited the optimum combination of enhanced Neu5Gc vs Neu5Ac discrimination and the capacity to recognise both α2-3- and α2-6-linked Neu5Gc structures. The SubB$_{ΔT107/ΔE108}$ deletion mutant bound α2-6-linked N-glycolylneuraminic acid glycans with substantially greater affinity than wild-type SubB protein, while also binding α2-3-linked N-glycolylneuraminic acid glycans. However, in contrast to SubB$_{ΔS106/ΔT107}$, SubB$_{ΔT107/ΔE108}$ can broadly bind Neu5Ac glycans such as Neu5Ac-α2-6-lac, which are not detectably bound by either wild-type SubB or SubB$_{ΔS106/ΔT107}$.

The anti-Neu5Gc antibody produced in chicken was used as a control and showed less selectivity and lower affinity for Neu5Gc containing glycans than any of the SubB proteins tested.

Glycan Array Analysis of Wild-Type SubB, SubBS106A/T107A and SubBΔS106/ΔT107.

To assess whether the preferred, Neu5Gc-specific SubBΔS106/ΔT107 mutation introduced specificity for non-sialylated structures, not covered by the SPR analysis, glycan array analysis was performed on the SubB wild-type, SubBΔS106/ΔT107 and SubBS106A/T107A mutants (Table 4). Wild-type SubB displayed significant binding to only four of 402 structures on the glycan array; Neu5Gcα2-3 Gal, Neu5Gcα2-3 Galβ1-4GlcNAc and two Neu5Acα2-3Galβ1-4GlcNAc terminated structures. This is in agreement with previously published glycan array analysis of SubB8 (functionalglycomics.org/glycomics/HServlet?operation=view&sideMenu=no&psId=primscreen_1579 #). SubBΔS106/ΔT107 only had displayed significant binding to four structures on the array. These were limited to structures terminating with Neu5Gcα2-3Gal or Neu5Gcα2-6 Gal. SubBS106A/T107A bound to 18 glycans in total on the array including structures containing Neu5Gc and Neu5Ac. It also recognised sulfated structures including glycosaminoglycans (heparin and chondroitin-6-sulfate) and sulfated lactosamine structures (Table 4). SubBS106A/T107A also recognised a range negatively charged of monosaccharides (Neu5Ac, Neu5Gc, 9-NAc-Neu5Ac, 3-O-Su-GlcNAc) on the array.

ELISA of Engineered SubB Against Human and Bovine Proteins/Serum

Figure 3:
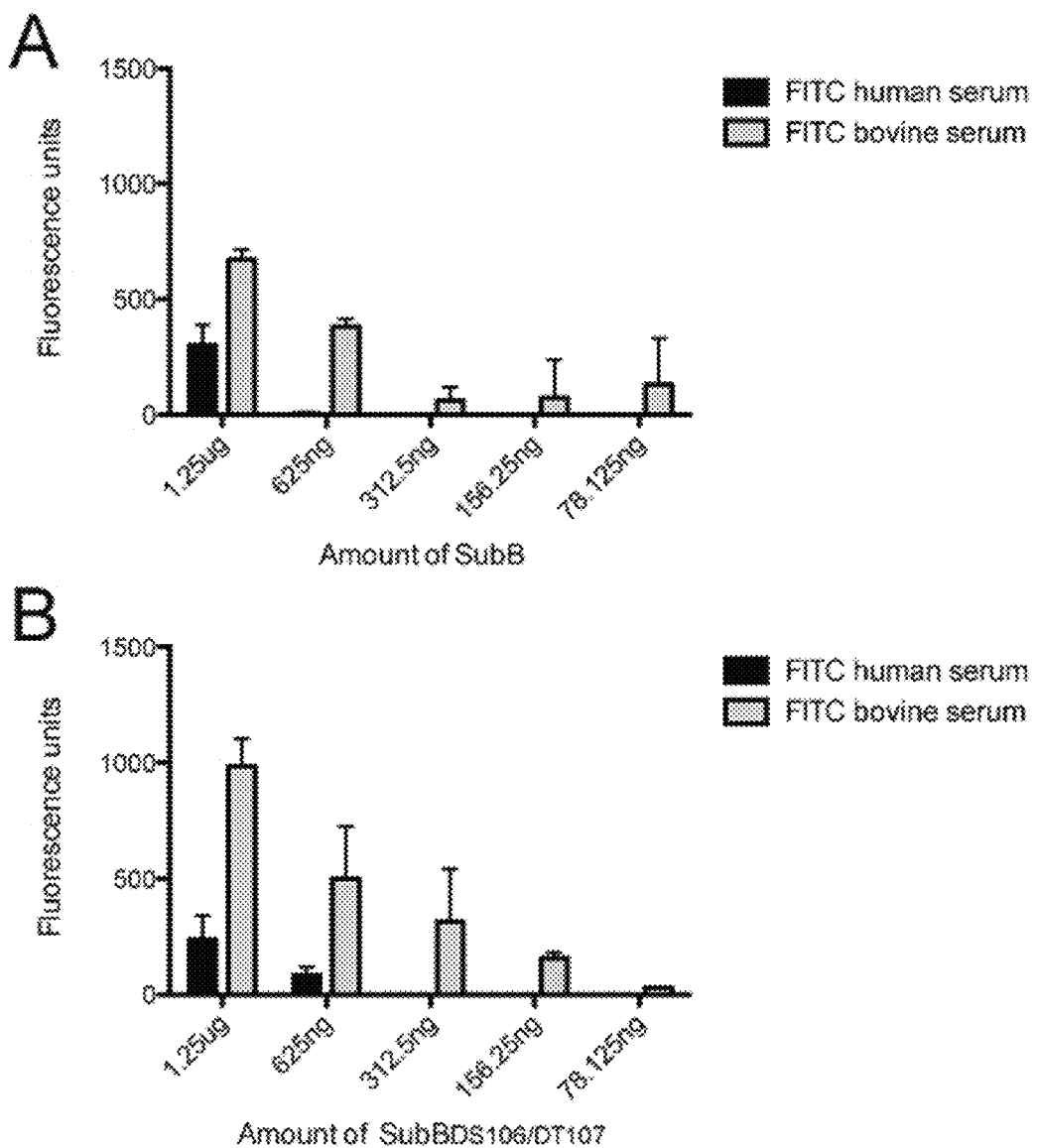
FIG. 3. ELISA of engineered SubB against FITC-labelled human and bovine serum. SubB (A) and SubB$_{\Delta S106/\Delta T107}$ (B) coated onto ELISA plates was able to capture FITC-labelled human and bovine serum proteins. Error bars show +1SD from the mean of duplicate assays.

To assess the ability of the engineered mutants to detect the presence of Neu5Gc in biological samples ELISA assays were performed. Using dishes coated with a dilution series of SubB, labelled serum proteins from human and bovine sources were tested. A two-fold improvement in differential recognition of the Neu5Gc containing serum proteins from bovine was identified with SubB$_{ΔS106/ΔT107}$. (FIG. 3).

Detection of Human Vs Bovine AGP

Figure 4:
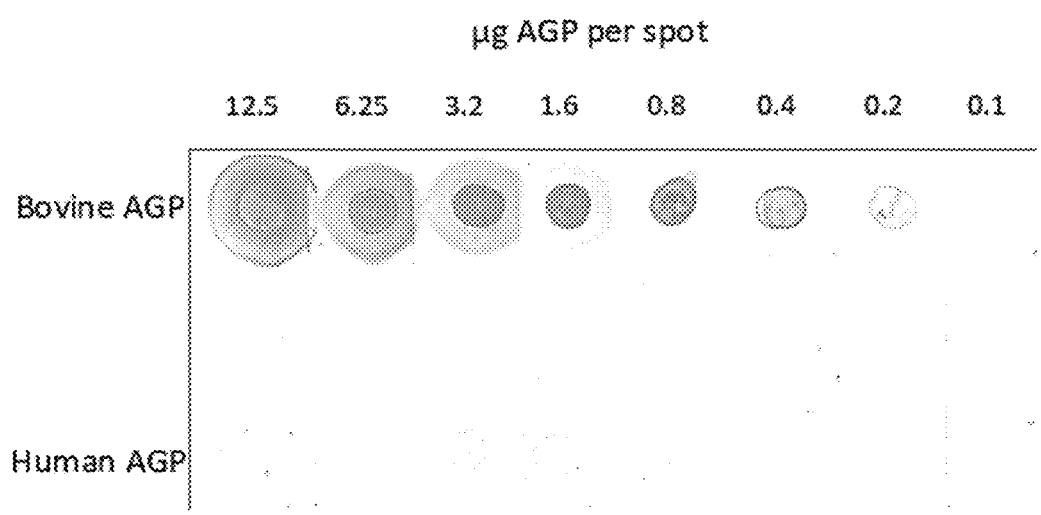
FIG. 4. Lectin overlay assay. Binding of SubB$_{\Delta S106/\Delta T107}$ to serial dilutions of human or bovine AGP spotted onto nitrocellulose (total amounts of protein per spot indicated).

To independently verify the capacity to discriminate between human and bovine AGP (only bovine AGP displays significant levels of Neu5Gc-terminating glycans), serially diluted glycoproteins were spotted onto nitrocellulose filters and after washing and blocking, filters were overlayed with purified biotinylated SubB$_{ΔS106/ΔT107}$. Bound lectin was then detected on washed filters using Streptavidin-AP (FIG. 4). SubB$_{ΔS106/ΔT107}$ binding to bovine AGP was detectable down to approximately 200 ng/spot, while significant binding to human AGP was not detectable even at the maximum amount tested (12.5 μg/spot). This discriminatory power is consistent with the SPR data above.

Additional Glycan Arrays

Figure 6:
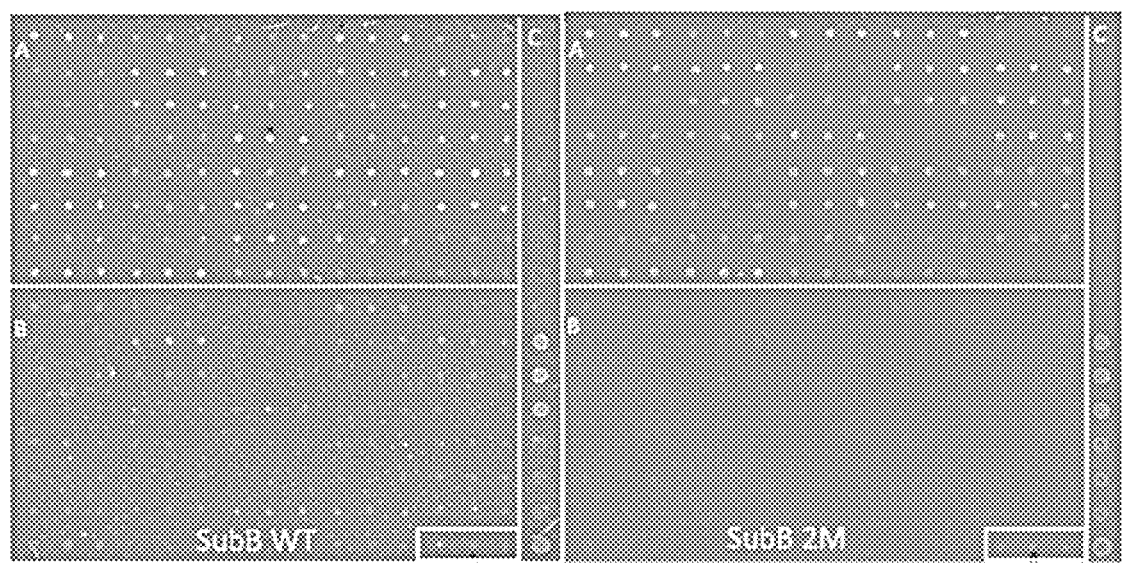
FIG. 6. SubB wild-type (WT) and SubB ΔS106/ΔT107 (residues 129 and 130 of SEQ ID NO:2) deletion mutant (2M) raw images of the Z-biotech arrays. Region A (Top and 3 spots at bottom right of each subarray) Neu5Gc Glycans. Region B (Bottom of each subarray) Neu5Ac glycans. Region C (Right side of each subarray) Control spots.
Figure 7:
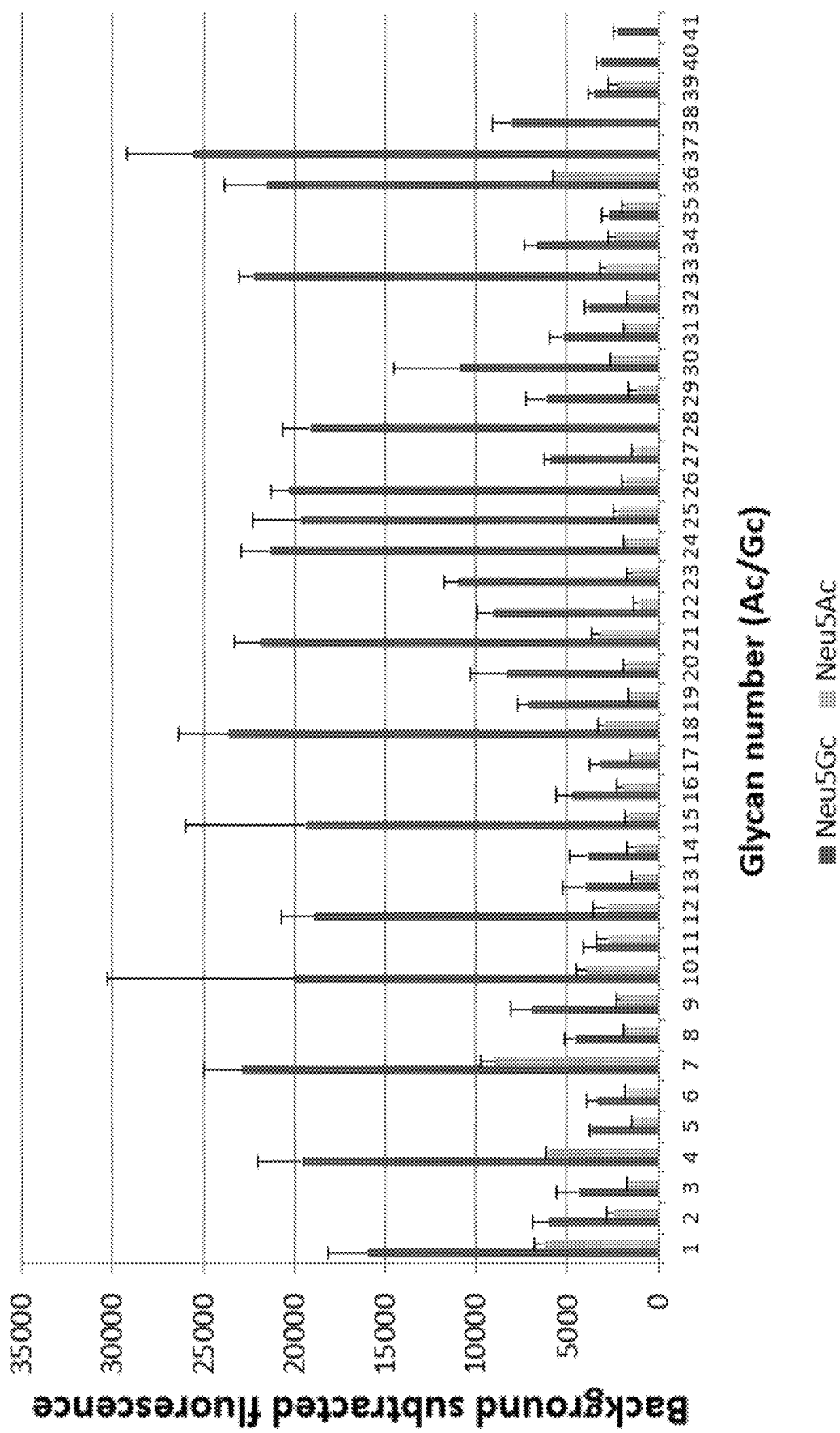
FIG. 7. SubB WT interaction with the Z-Biotech Neu5Ac/Gc glycan array. Neu5Gc glycans are shown in blue, Neu5Ac are shown in red.
Figure 8:
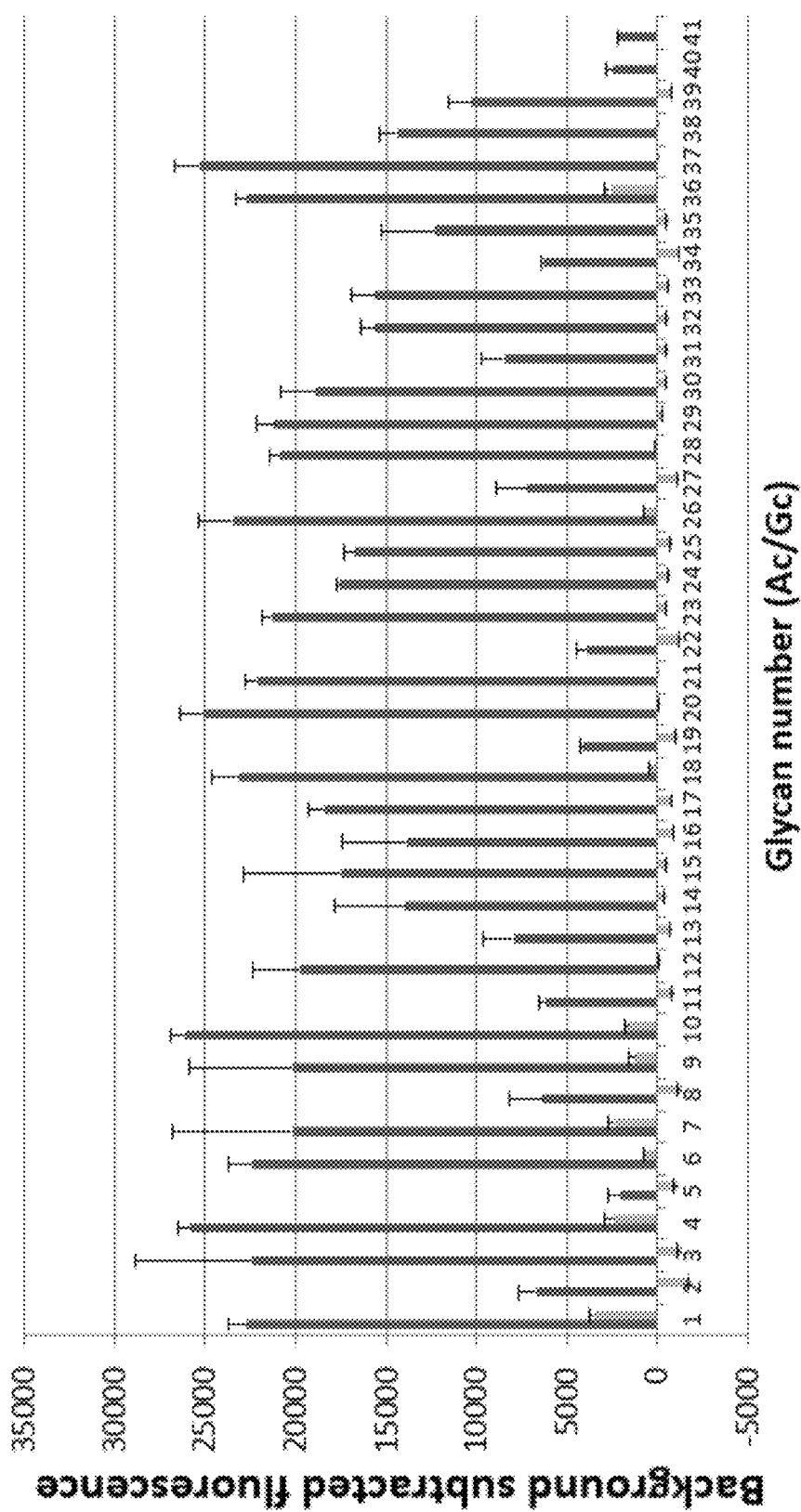
FIG. 8. SubB ΔS106/ΔT107 (residues 129 and 130 of SEQ ID NO:2) deletion mutant (Sub2M) interaction with the Z-Biotech Neu5Ac/Gc glycan array. Neu5Gc glycans are shown in blue, Neu5Ac are shown in red.
Figure 9:
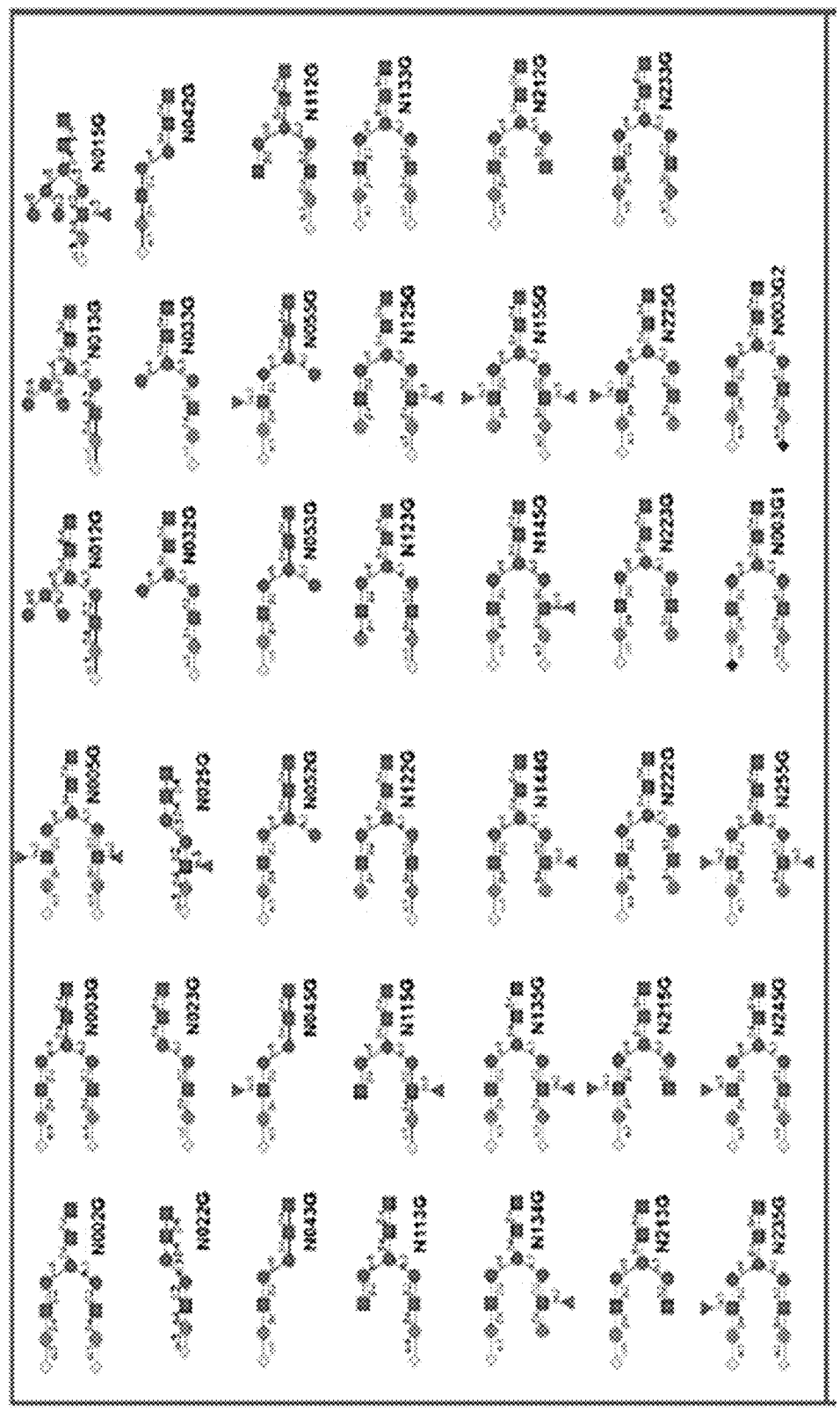
FIG. 9. Glycans on the Z-biotech array.
Figure 9:
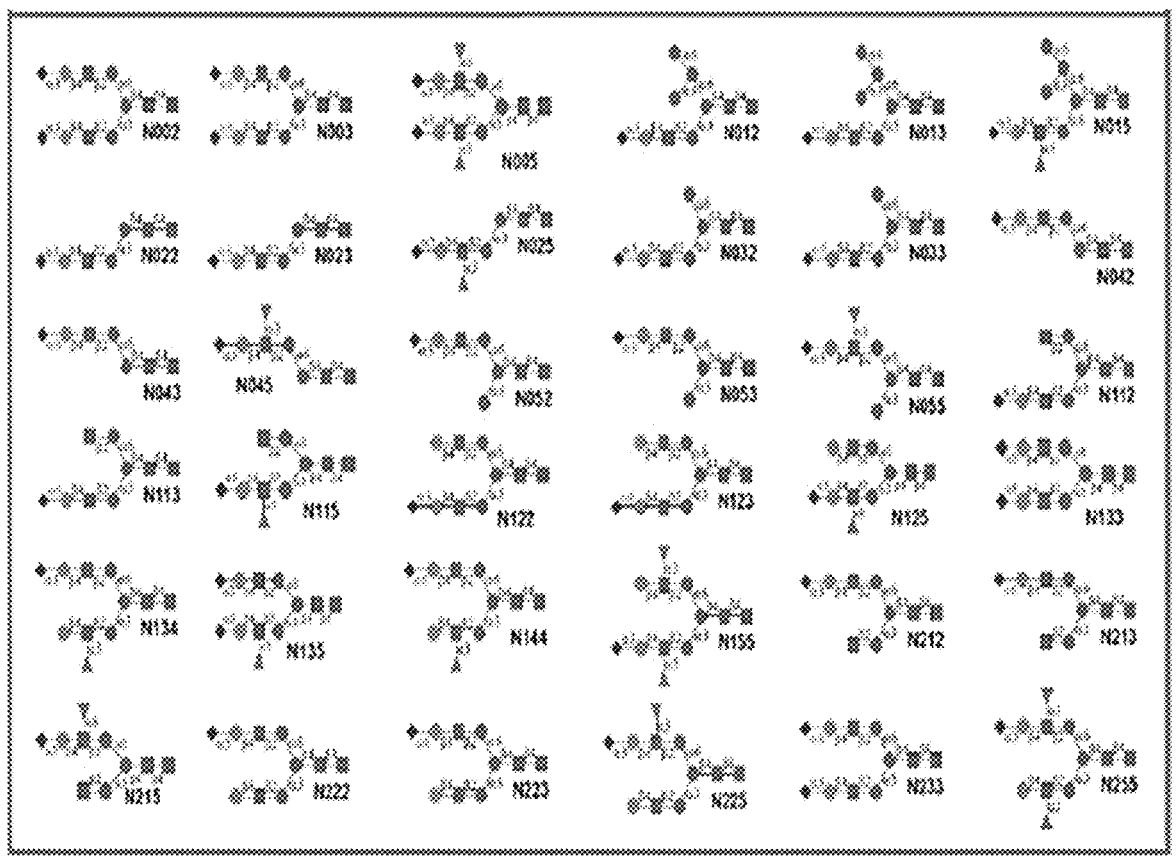

The various Neu5Ac and Neu5Gc glycan structures analysed in the Z-biotech glycan arrays are shown in FIG. 9 and an example of an array in FIG. 6. Table 3 provides the code linking the glycans of FIG. 9 with the array data in FIGS. 7 and 8. The array data summarized in FIG. 7 show that binding to Neu5Gc structures is preferred by the wild-type SubB but there are 4/40 Neu5Ac glycans that are bound with greater than 5000 fluorescence units above background and 14/41 Neu5Gc structures that have binding below 5000. All Neu5Ac structures register some binding above background.

As also evident in FIG. 8, binding to Neu5Gc structures is preferred by SubB 2M. No Neu5Ac glycans are bound with greater than 5000 fluorescence units above background and only 5/41 Neu5Gc structures that have binding below 5000. Only 7/14 Neu5Ac glycans have any binding above background. This results shows a definitive improvement over the results obtained with the WT SubB in terms of specificity for Neu5Gc and improved recognition of different linkages and presentations of Neu5Gc containing glycans.

Further Development of the on Chip Screening of Neu5Gc Containing Proteins in Serum Using SubB 2M.

Figure 10:
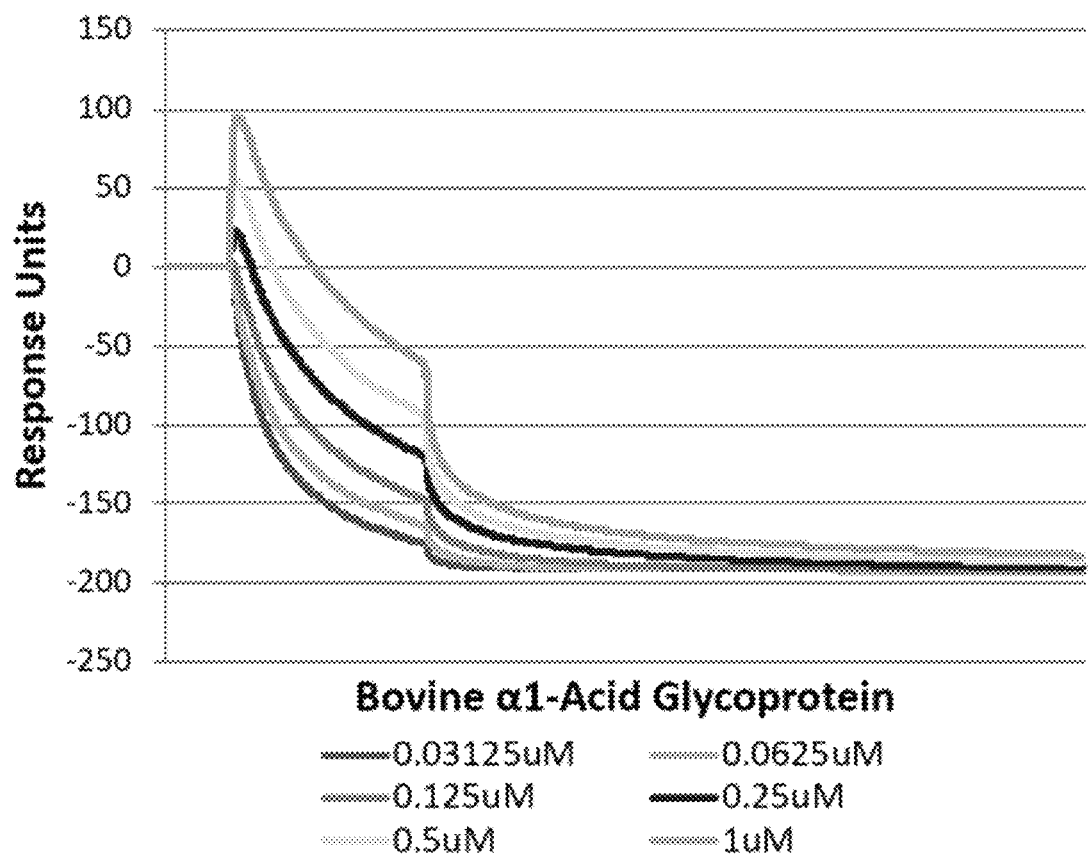
FIG. 10. SubB WT with bovine AGP spiked into 1% normal human serum.
Figure 11:
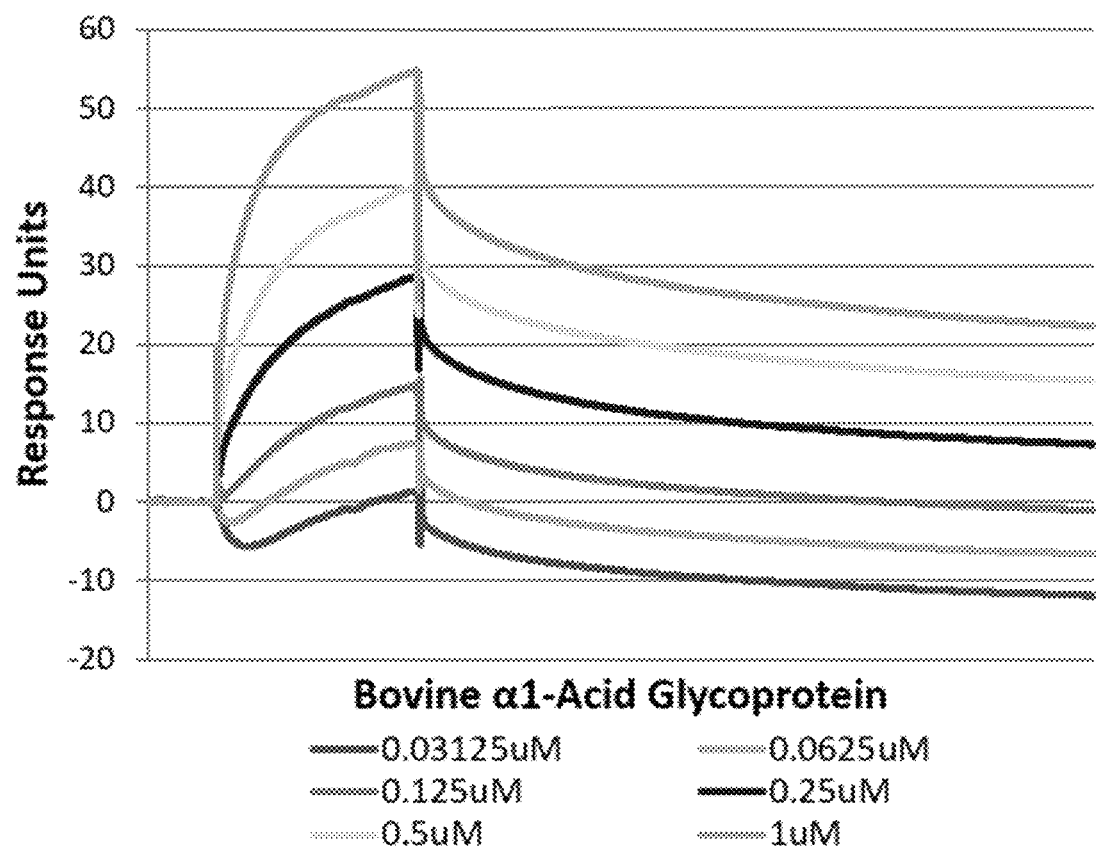
FIG. 11. SubB 2M (ΔS106/ΔT107 (residues 129 and 130 of SEQ ID NO:2) deletion mutant) with bovine AGP spiked into 1% normal human serum.

Referring to FIGS. 10 and 11, all assays were performed in a background of 1% normal human serum obtained from Sigma-Aldrich. The wild-type SubB was unable to be analysed as all binding observed resulting from the serum present with values dropping below the serum only control when a Neu5Gc containing protein was spiked. This indicates that the SubB WT had preference for the Neu5Gc protein over the serum but bound the serum at high levels in the absence of the protein (FIG. 10). In FIG. 11, the SubB 2M performed much better with responses above the serum background from concentrations between 31.25 nM and 62.5 nM. This is at a protein concentration of ~2 µg/mL.

Discussion

Neu5Gc is an important diagnostic and prognostic marker in human carcinomas, with elevated Neu5Gc expression detected in breast, ovarian, prostate, colon and lung cancer[11,12]. Wild-type SubB had unprecedented specificity for glycans terminating in Neu5Gc, but bound poorly to α2-6-linked Neu5Gc and still recognised α2-3-linked Neu5Ac structures albeit weakly[8]. To improve the recognition of SubB for α2-6-linked Neu5Gc and make it more specific for Neu5Gc, we engineered SubB using structure-aided modifications, with specific focus on the T104-E108 loop.

Manipulation of this loop had two specific outcomes through the modification of the same two amino acids. Firstly, alanine substitution of S106 and T107 (S106A/T107A (residues 129-130 of SEQ ID NO:2)) led to a loss of specificity for Neu5Gc, producing a lectin capable of binding to all tested terminally sialylated glycans regardless of linkage (α2-3 and α2-6) or sialic acid type (Neu5Ac or Neu5Gc). The second was that deletion of the same two amino acids (ΔS106/ΔT107 (residues 129-130 of SEQ ID NO:2)) produced a lectin with exquisite specificity for Neu5Gc regardless of linkage (α2-3 and α2-6). The $SubB_{\Delta S106/\Delta T107}$ mutant was significantly improved for the recognition Neu5Gc containing structures compared to the wild-type SubB. $SubB_{\Delta S106/\Delta T107}$ also had no difference in its ability to bind α2-3-linked Neu5Gc or α2-6-linked Neu5Gc structures, making it a significant improvement over the wild-type protein. Further modifications of the SubB protein outside of the S106 and T107 amino acids (residues 129-130 of SEQ ID NO:2) produced no significant improvement in specificity. The $SubB_{\Delta S106/\Delta T107/E108D}$ mutant protein, which is the $SubB_{\Delta S106/\Delta T107}$ protein with a E108D (residue 131 of SEQ ID NO:2) mutation also added, was less able to distinguish α2-3-linked Neu5Gc from α2-3-linked Neu5Ac than $SubB_{\Delta S106/\Delta T107}$ and had stronger binding to the human α1-Acid glycoprotein than the $SubB_{\Delta S106/\Delta T107}$ mutant (24 fold more protein bound by $SubB_{\Delta S106/\Delta T107/E108D}$ than $SubB_{\Delta S106/\Delta T107}$). In contrast, the $SubB_{\Delta T107/E108}$ deletion mutant not only bound α2-6-linked N-glycolylneuraminic acid glycans and α2-3-linked N-glycolylneuraminic acid glycans but also Neu5Ac glycans such as Neu5Ac-α2-6-lac and Neu5Ac-α2-3-lac, which are not detectably bound by $SubB_{\Delta S106/\Delta T107}$.

These improved SubB mutants offer a new tool for the testing of biological samples, particularly serum and other fluids from individuals with cancer or suspected of having cancer.

Methods

Structural Modeling of SubB.

The three-dimensional structure of the SubB mutants were modeled using Phyre2[24]. Neu5GCα2-6Galβ1-3Glc was acquired from PDB ID: 4EN8[25] and modeled into the SubB and SubB mutant structures manually using Coot[26].

Construction and Expression of SubB Mutants.

Mutations were introduced into the subB coding sequence (close to the 3' end) by direct high-fidelity PCR using the forward primer pETSubBF and the respective mutant-specific reverse primers listed in Table 2. PCR products were cloned into the BamHI and XhoI sites of pET-23(+) (Novagen) and transformed into E. coli. BL21(DE3). SubB derivatives were expressed and purified as $His_6$-tagged fusion proteins by Ni-NTA affinity chromatography, as previously described[4]. Proteins were >95% pure as judged by SDS-PAGE and Coomassie blue staining.

Surface Plasmon Resonance of SubB and Engineered SubB Mutants.

Surface Plasmon resonance (SPR) was run using the Biacore T100 system (GE) as described previously[27]. Briefly, SubB, SubB mutants and anti-Neu5Gc IgY (SiaMab; formerly Sialix/GC-Free Inc., San Diego, Calif., USA) were immobilized onto flow cell 2-4 of a series S sensor chip CM5 (GE) using the NHS capture kit and flow cell 1 was run as a blank immobilization. Monosaccharides, disaccharides, oligosaccharides and α1-Acid glycoprotein from human and bovine sources (Sigma-Aldrich; See Table 1) were flowed over at 0.01-100 µM on initial range finding experiments. Concentrations were adjusted and all data were analysed using single cycle kinetics using the Biacore T100 Evaluation software.

Mass Spectroscopic Analysis of α1-Acid Glycoprotein.

AGP from human plasma (Sigma-Aldrich G9885) and bovine plasma (Sigma-Aldrich G3643) (1 mg in 6M guanidinium chloride, 50 mM Tris-HCl pH8) was reduced and alkylated with 10 mM dithiothreitol and 25 mM acrylamide, respectively. Protein was then precipitated by adding 4 volumes of 1:1 methanol:acetone, incubating in −20° C. for 16 h and then centrifuged (18,000 rcf, 10 min) to collect the pellet. The precipitated protein was resuspended in 50 µL of 50 mM Tris-HCl pH8 and digested (37° C., 16 h) with 1 µg trypsin (Trypsin Gold, Promega). Digested peptides were then desalted with C18 ZipTips (Millipore).

ELISA Analysis of SubB and the Engineered $SubB_{\Delta S106/\Delta T107}$ Mutant.

Wells of black 96-well NUNC Maxisorp plates were coated with SubB or $SubB_{\Delta S106/\Delta T107}$ protein two-fold serially diluted in 100 mM bicarbonate/carbonate coating buffer (pH9.6) starting at 1.25 µg of protein overnight at 4° C. Wells were washed 3 times with phosphate-buffered saline, 0.05% Tween-20 (PBS-T) before blocking solution (3% BSA) was added for 1 hour at room temperature. Proteins in normal human serum and bovine serum were fluorescently labelled by combining neat serum with 100 µM FITC dye (Peirce) and incubating on ice for 1 hour. Excess dye was removed using a 1 kDa size exclusion spin column. 100 µl of FITC-labelled normal human serum or bovine serum was added to wells coated with SubB or $SubB_{\Delta S106/\Delta T107}$ and wells were incubated for 1 hour at room temperature. Wells were washed 3 times with PBS-T. 100 µl of PBS was added to each well before the fluorescence was measured at 485/535 nm. Fluorescence unit values are shown as the mean of duplicates+/−SD, with the mean fluorescence units obtained for wells containing all reagents except for the SubB proteins subtracted. Any negative value was considered as 0.

SubB Overlay Experiments.

Purified SubB$_{AS106/AT107}$ was labelled with biotin using the EZ-LinV Sulfo-NHS-Biotinylation Kit (Thermo Scientific) according to the manufacturer's instructions. Purified human and bovine α-1 acid glycoprotein (Sigma cat. nos. G9885 and G3643) were dissolved in water at 5 mg/ml and 5 μl volumes of serial two-fold dilutions were spotted onto nitrocellulose filters and air dried at 37° C. overnight. Filters were then blocked with 5% skim milk in Tris-buffered saline with 0.05% Tween 20 (TTBS) for 2 h. After washing three times in TTBS, filters were overlaid with 1 μg/ml biotin-SubB$_{AS106/AT107}$ in TTBS and incubated overnight at 4° C. Filters were then washed three times in TTBS and bound biotin-SubB$_{AS106/AT107}$ was detected using streptavidin-alkaline phosphatase conjugate (Roche). Filters were developed using a chromogenic nitro-blue tetrazolium/X-phosphate substrate system (Roche).

Glycan Array Analysis of SubB and Engineered SubB Mutants.

For the data shown in Table 3, glycan array slides were printed on SuperEpoxy 3 (Arrayit) activated substrates using an Arrayit Spotbot Extreme contact printer as previously described[28]. For each subarray 2 μg of SubB proteins were pre-complexed with anti-His tag antibody (Cell signalling) and Alexa555 secondary and tertiary antibodies (rabbit anti-mouse; goat anti-rabbit) at a ratio of 2:1:0.5:0.25 in a final volume of 500 μL. This 500 μL antibody protein complex was added to a 65 μL gene frame (Thermo Scientific) without a coverslip. Washing and analysis was performed as previously described[27].

Neu5Ac/Neu5Gc Glycan Arrays

For the data shown in FIGS. 6-9, Neu5Ac/Neu5Gc Glycan arrays were obtained from Z-biotech (zbiotech.com/neu5gc-xenoantigen-microarray.html). Arrays were preformed as per manufacturer's instructions with a total of 2 μg of protein applied to each of the subarray areas. Detection was with mouse anti-His IgG (1:1 molar ratio with protein), rabbit anti-mouse Alexa 555 IgG (0.5 molar amount of mouse IgG) and goat anti-rabbit Alexa 555 IgG (0.5 molar amount of rabbit IgG). Proteins were incubated for 1 hour and washed 3 times in 1×PBS. Slides were scanned on an Innoscan 1100AL using 488, 532 and 647 lasers. Arrays were analysed with Mapix software. All data was taken from the 532 laser channel and background subtracted fluorescence was used in the analysis.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. Beddoe, T., Paton, A. W., Le Nours, J., Rossjohn, J. & Paton, J. C. Structure, biological functions and applications of the AB5 toxins. *Trends Biochem Sci* 35, 411-8 (2010).
2. Petr, T. et al. Histochemical detection of GM1 ganglioside using cholera toxin-B subunit. Evaluation of critical factors optimal for in situ detection with special emphasis to acetone pre-extraction. *Eur J Histochem* 54, e23 (2010).
3. Kenworthy, A. K., Petranova, N. & Edidin, M. High-resolution FRET microscopy of cholera toxin B-subunit and GPI-anchored proteins in cell plasma membranes. *Mol Biol Cell* 11, 1645-55 (2000).
4. Paton, A. W., Srimanote, P., Talbot, U. M., Wang, H. & Paton, J. C. A new family of potent AB(5) cytotoxins produced by Shiga toxigenic *Escherichia coli*. *J Exp Med* 200, 35-46 (2004).
5. Paton, A. W. et al. AB5 subtilase cytotoxin inactivates the endoplasmic reticulum chaperone BiP. *Nature* 443, 548-52 (2006).
6. Backer, J. M. et al. Chaperone-targeting cytotoxin and endoplasmic reticulum stress-inducing drug synergize to kill cancer cells. *Neoplasia* 11, 1165-73 (2009).
7. Martin, S. et al. Targeting GRP78 to enhance melanoma cell death. *Pigment Cell Melanoma Res* 23, 675-82 (2010).
8. Byres, E. et al. Incorporation of a non-human glycan mediates human susceptibility to a bacterial toxin. *Nature* 456, 648-52 (2008).
9. Inoue, S., Sato, C. & Kitajima, K. Extensive enrichment of N-glycolylneuraminic acid in extracellular sialoglycoproteins abundantly synthesized and secreted by human cancer cells. *Glycobiology* 20, 752-62 (2010).
10. Malykh, Y. N., Schauer, R. & Shaw, L. N-Glycolylneuraminic acid in human tumours. *Biochimie* 83, 623-34 (2001).
11. Marquina, G. et al. Gangliosides expressed in human breast cancer. *Cancer Res* 56, 5165-71 (1996).
12. Samraj, A. N., Laubli, H., Varki, N. & Varki, A. Involvement of a non-human sialic Acid in human cancer. *Front Oncol* 4, 33 (2014).
13. Varki, N. M. & Varki, A. Diversity in cell surface sialic acid presentations: implications for biology and disease. *Lab Invest* 87, 851-7 (2007).
14. Lofling, J. C., Paton, A. W., Varki, N. M., Paton, J. C. & Varki, A. A dietary non-human sialic acid may facilitate hemolytic-uremic syndrome. *Kidney Int* 76, 140-4 (2009).
15. Yin, J. et al. Hypoxic culture induces expression of sialin, a sialic acid transporter, and cancer-associated gangliosides containing non-human sialic acid on human cancer cells. *Cancer Res* 66, 2937-45 (2006).
16. Dennis, J. W., Laferte, S., Yagel, S. & Breitman, M. L. Asparagine-linked oligosaccharides associated with metastatic cancer. *Cancer Cells* 1, 87-92 (1989).
17. Padler-Karavani, V. et al. Human xeno-autoantibodies against a non-human sialic acid serve as novel serum biomarkers and immunotherapeutics in cancer. *Cancer Res* 71, 3352-63 (2011).
18. Pham, T. et al. Evidence for a novel human-specific xeno-auto-antibody response against vascular endothelium. *Blood* 114, 5225-35 (2009).
19. Murayama, T. et al. Colon carcinoma glycoproteins carrying alpha 2,6-linked sialic acid reactive with *Sambucus nigra* agglutinin are not constitutively expressed in normal human colon mucosa and are distinct from sialyl-Tn antigen. *Int J Cancer* 70, 575-81 (1997).
20. Sata, T., Roth, J., Zuber, C., Stamm, B. & Heitz, P. U. Expression of alpha 2,6-linked sialic acid residues in neoplastic but not in normal human colonic mucosa. A lectin-gold cytochemical study with *Sambucus nigra* and *Maackia amurensis* lectins. *Am J Pathol* 139, 1435-48 (1991).

21. Hedlund, M., Ng, E., Varki, A. & Varki, N. M. alpha 2-6-Linked sialic acids on N-glycans modulate carcinoma differentiation in vivo. *Cancer Res* 68, 388-94 (2008).
22. Imre, T. et al. Glycosylation site analysis of human alpha-1-acid glycoprotein (AGP) by capillary liquid chromatography-electrospray mass spectrometry. *J Mass Spectrom* 40, 1472-83 (2005).
23. Nakano, M., Kakehi, K., Tsai, M. H. & Lee, Y. C. Detailed structural features of glycan chains derived from alpha1-acid glycoproteins of several different animals: the presence of hypersialylated, 0-acetylated sialic acids but not disialyl residues. *Glycobiology* 14, 431-41 (2004).
24. Kelley, L. A., Mezulis, S., Yates, C. M., Wass, M. N. & Sternberg, M. J. The Phyre2 web portal for protein modeling, prediction and analysis. *Nat Protoc* 10, 845-58 (2015).
25. Yamashita, S. et al. Carbohydrate recognition mechanism of HA70 from *Clostridium botulinum* deduced from X-ray structures in complexes with sialylated oligosaccharides. *FEBS Lett* 586, 2404-10 (2012).
26. Emsley, P., Lohkamp, B., Scott, W. G. & Cowtan, K. Features and development of Coot. *Acta Cystallogr D Biol Crystallogr* 66, 486-501 (2010).
27. Shewell, L. K. et al. The cholesterol-dependent cytolysins pneumolysis and streptolysin O require binding to red blood cell glycans for hemolytic activity. *Proc Natl Acad Sci USA* 111, E5312-20 (2014).

TABLE 1

Surface Plasmon Resonance analysis of Neu5Gc binding proteins

| SubB variant/ antibody | Human α1-AGP | Bovine α1-AGP | Neu5Ac- α2-3-lac | Neu5Gc- α2-3-lac | Neu5Ac- α2-6-lac | Neu5Gc- α2-6-lac | Free Neu5Ac |
|---|---|---|---|---|---|---|---|
| Anti-Neu5Gc antibody (IgY IgY) | n.t. | n.t. | 249 ± 46 μm | 2.34 ± 0.85 μm | n.t. | n.t. | NCDI |
| Wild type SubB | 2.12 ± 0.56 μM (Rmax = 125) | 155.8 ± 22 nM (Rmax = 525) | 2.24 ± 0.93 μM | 6.62 ± 2.17 nM | NCDI | NCDI | NCDI |
| S106A/ T107A | 723 ± 129 nM (Rmax = 142) | 164 ± 10 nM (Rmax = 499) | 489 ± 171 nM | 1.52 ± 0.50 nM | 348 ± 52 nM | 8.05 ± 0.14 nM | 3.27 ± 0.29 μM |
| T107A | n.t. | n.t. | 4.18 ± 1.6 μM | 15.2 ± 0.02 nM | NCDI | 208 ± 123 nM | NCDI |
| ΔS106/ ΔT107 | 1.65 ± 0.42 μM (Rmax = 7) | 115 ± 37 nM (Rmax = 299) | NCDI | 15.3 ± 5.8 nM | NCDI | 8.53 ± 0.15 nM | NCDI |
| ΔS106/ ΔT107/ E108D | 2.82 ± 0.15 μM (Rmax = 165) | 32.5 ± 2.6 nM (Rmax = 276) | 371 ± 64 nM | 7.39 ± 0.72 nM | NCDI | 3.45 ± 0.87 nM | NCDI |
| ΔT107/ ΔE108 | 308 ± 24 nM (Rmax = 542)** | 98.8 ± 43 nM (Rmax = 865)** | 9.65 ± 0.70 nM | 4.32 ± 0.65 nM | 4.94 ± 0.35 nM | 3.71 ± 0.41 nM | n.t. |
| ΔS106/ ΔT107/ ΔE108* | n.t. | n.t. | n.t. | n.t. | n.t. | n.t. | n.t. |

| SubB variant/ antibody | Free Neu5Gc | Man5 | maltose | Lactose | GT2 | Chondroitin 6 sulfate |
|---|---|---|---|---|---|---|
| Anti-Neu5Gc antibody (IgY IgY) | 35.7 ± 4.2 μm | n.t. | n.t. | n.t. | n.t. | n.t. |
| Wild type SubB | 18.1 ± 5.9 nM | NCDI | NCDI | NCDI | NCDI | NCDI |
| S106A/ T107A | 6.61 ± 1.6 nM | NCDI | NCDI | NCDI | 8.97 ± 2.2 μM | 33.0 ± 7.6 μM |
| T107A | 16.8 ± 0.99 nM | n.t. | n.t | n.t. | n.t. | n.t. |
| ΔS106/ ΔT107 | 17.8 ± 4.0 nM | NCDI | NCDI | NCDI | NCDI | NCDI |
| ΔS106/ ΔT107/ E108D | 45.1 ± 1.2 nM | n.t. | n.t. | n.t. | n.t. | n.t. |
| ΔT107/ ΔE108 | n.t. | n.t. | n.t. | n.t. | n.t. | n.t. |
| ΔS106/ ΔT107/ ΔE108* | n.t. | n.t. | n.t. | n.t. | n.t. | n.t. |

*Protein insoluble
**Performed on a different occasion. Captured 3 fold additional protein compared to the previous protein.

Table 1 legend:

Binding affinities of wild type SubB, various mutant derivatives and an anti-Neu5Gc IgY antibody, to purified tri- and monosaccharides and/or human or bovine α1-acid glycoprotein (AGP) was determined by SPR, as described in the Materials and Methods.
NCDI indicates that no concentration-dependent interaction was observed with concentrations ranging up to 100 μM;
ND: Not done;
Rmax:the total amount of response units (RUs) of the analyte bound to the protein (the higher the number the more the glycan/glycoprotein was bound by the immobilised SubB).

TABLE 2

Oligonucleotides

| Primer | Sequence 5'-3' |
|---|---|
| pETSubBF | TTGTAAGGATCCGGAGGTGCATATGACG (SEQ ID NO: 4) |
| pETSubB$_{T107A}$R | GATTATCTCGAGTGAGTTCTTTTTCCTGTCAGGACCAAAACATTCTGCCGATGTGGTGCAGGTTG (SEQ ID NO: 5) |
| pETSubB$_{S106A/T107A}$R | GATTATCTCGAGTGAGTTCTTTTTCCTGTCAGGACCAAAACATTCTGCCGCTGTGGTGCAGGTTG (SEQ ID NO: 6) |
| pETSubB$_{\Delta S106/\Delta T107}$R | GATTATCTCGAGTGAGTTCTTTTTCCTGTCAGGACCAAAACATTCTGTGGTGCAGGTTGATAACCC (SEQ ID NO: 7) |
| pETSubB$_{\Delta S106/\Delta T107/E108D}$R | GATTATCTCGAGTGAGTTCTTTTTCCTGTCAGGACCAAAACAGTCTGTGGTGCAGGTTGATAACCC (SEQ ID NO: 8) |

TABLE 3

Glycan codes for FIGS. 7-9

| Gc Glycan ID | Neu5Gc Glycans | Ac Glycan ID | Neu5Ac Glycans |
|---|---|---|---|
| GC-1 | N002G | AC-1 | N002 |
| GC-2 | N003G | AC-2 | N003 |
| GC-3 | N005G | AC-3 | N005 |
| GC-4 | N012G | AC-4 | N012 |
| GC-5 | N013G | AC-5 | N013 |
| GC-6 | N015G | AC-6 | N015 |
| GC-7 | N022G | AC-7 | N022 |
| GC-8 | N023G | AC-8 | N023 |
| GC-9 | N025G | AC-9 | N025 |
| GC-10 | N032G | AC-10 | N032 |
| GC-11 | N033G | AC-11 | N033 |
| GC-12 | N042G | AC-12 | N042 |
| GC-13 | N043G | AC-13 | N043 |
| GC-14 | N045G | AC-14 | N045 |
| GC-15 | N052G | AC-15 | N052 |
| GC-16 | N053G | AC-16 | N053 |
| GC-17 | N055G | AC-17 | N055 |
| GC-18 | N112G | AC-18 | N112 |
| GC-19 | N113G | AC-19 | N113 |
| GC-20 | N115G | AC-20 | N115 |
| GC-21 | N122G | AC-21 | N122 |
| GC-22 | N123G | AC-22 | N123 |
| GC-23 | N125G | AC-23 | N125 |
| GC-24 | N133G | AC-24 | N133 |
| GC-25 | N134G | AC-25 | N134 |
| GC-26 | N135G | AC-26 | N135 |
| GC-27 | N144G | AC-27 | N144 |
| GC-28 | N145G | | |
| GC-29 | N155G | AC-29 | N155 |
| GC-30 | N212G | AC-30 | N212 |
| GC-31 | N213G | AC-31 | N213 |
| GC-32 | N215G | AC-32 | N215 |
| GC-33 | N222G | AC-33 | N222 |
| GC-34 | N223G | AC-34 | N223 |
| GC-35 | N225G | AC-35 | N225 |
| GC-36 | N233G | AC-36 | N233 |
| GC-37 | N235G | | |
| GC-38 | N245G | | |
| GC-39 | N255G | AC-39 | N255 |
| GC-40 | N003G1 | | |
| GC-41 | N003G2 | | |

TABLE 4

| | | Average Fold value above background (Ave background + 3x Standard Error of the Mean) | | |
|---|---|---|---|---|
| Number | Structure | SubB WT | SubBΔS106/ΔT107 | SubBS106A/T107A |
| MONOSACCHARIDES | | | | |
| 1 | Fucα-sp3 | −0.003 | 0.119 | 0.250 |
| 2 | Galα-sp3 | −0.533 | 0.117 | 0.058 |
| 3 | Galβ-sp3 | 0.000 | 0.167 | 0.109 |
| 4 | GalNAcα-sp0 | −0.006 | 0.253 | 0.168 |
| 5 | GalNAcα-sp3 | −0.010 | 0.531 | 0.445 |
| 6 | GalNAcβ-sp3 | 0.004 | 0.154 | 0.249 |
| 7 | Glcα-sp3 | 0.002 | 0.183 | 0.006 |
| 9 | Glcβ-sp3 | −0.001 | 0.156 | 0.767 |
| 10 | GlcNAcβ-sp3 | 0.001 | 0.128 | 0.748 |
| 14 | GlcN(Gc)β-sp4 | 0.006 | 0.153 | 0.423 |
| 15 | HOCH$_2$(HOCH)$_4$CH$_2$NH$_2$ | −0.011 | 0.103 | 0.119 |
| 16 | Manα-sp3 | 0.016 | 0.172 | 0.122 |
| 18 | Manβ-sp4 | −0.003 | 0.372 | 0.300 |
| 19 | ManNAcβ-sp4 | 0.021 | 0.086 | 0.056 |
| 20 | Rhaα-sp3 | 0.002 | 0.205 | 0.237 |
| 22 | GlcNAcβ-sp4 | −0.001 | 0.178 | 0.211 |
| 37 | 3-O-Su-Galβ-sp3 | −0.039 | 0.151 | 0.140 |
| 38 | 3-O-Su-GalNAcα-sp3 | −0.002 | 0.123 | 0.027 |
| 43 | 6-O-Su-GlcNAcβ-sp3 | −0.272 | 0.195 | 0.118 |
| 44 | GlcAα-sp3 | −0.022 | 0.120 | −0.308 |
| 45 | GlcAβ-sp3 | −0.009 | 0.306 | 0.100 |
| 46 | 6-H$_2$PO$_3$Glcβ-sp4 | 0.012 | 0.196 | 0.113 |
| 47 | 6-H$_2$PO$_3$Manα-sp3 | 0.000 | 0.223 | 0.040 |
| 48 | Neu5Acα-sp3 | 0.009 | 0.219 | 1.192 |

TABLE 4-continued

| Number | Structure | SubB WT | SubBΔS106/ΔT107 | SubBS106A/T107A |
|---|---|---|---|---|
| | | | Average Fold value above background (Ave background + 3x Standard Error of the Mean) | |
| 49 | Neu5Acα-sp9 | 0.002 | 0.137 | 1.848 |
| 52 | Neu5Gcα-sp3 | 0.004 | 0.163 | 2.205 |
| 54 | 9-NAc-Neu5Acα-sp3 | −0.020 | 0.108 | 1.292 |
| 55 | 3-O-Su-GlcNAcβ-sp3 | −0.001 | 0.131 | 1.403 |
| | Terminal Galactose | | | |
| 75 | Galα1-2Galβ-sp3 | −0.009 | 0.149 | 0.627 |
| 76 | Galα1-3Galβ-sp3 | 0.014 | 0.259 | 0.352 |
| 77 | Galα1-3GalNAcβ-sp3 | −0.004 | 0.127 | 0.466 |
| 78 | Galα1-3GalNAcα-sp3 | 0.008 | 0.174 | 0.335 |
| 80 | Galα1-3GlcNAcβ-sp3 | 0.009 | 0.129 | 0.119 |
| 81 | Galα1-4GlcNAcβ-sp3 | −0.004 | 0.131 | 0.213 |
| 83 | Galα1-6Glcβ-sp4 | 0.008 | 0.217 | 0.109 |
| 84 | Galβ1-2Galβ-sp3 | −0.024 | 0.139 | 0.056 |
| 85 | Galβ1-3GlcNaAcβ-sp3 | 0.043 | 0.071 | 0.052 |
| 87 | Galβ1-3Galβ-sp3 | 0.229 | 0.512 | 0.279 |
| 88 | Galβ1-3GalNAcβ-sp3 | 0.002 | 0.188 | 0.173 |
| 89 | Galβ1-3GalNAcα-sp3 | −0.003 | 0.134 | 0.240 |
| 93 | Galβ1-4Glcβ-sp4 | −0.004 | 0.131 | 0.158 |
| 94 | Galβ1-4Galβ-sp4 | −0.065 | 0.134 | 0.154 |
| 97 | Galβ1-4GlcNAcβ-sp3 | −0.004 | 0.143 | 0.095 |
| 100 | Galβ1-6Galβ-sp4 | 0.011 | 0.288 | 0.496 |
| 145 | Galβ1-3(6-O-Su)GlcNAcβ-sp3 | −0.016 | 0.310 | 0.674 |
| 146 | Galβ1-4(6-O-Su)Glcβ-sp2 | 0.085 | 0.187 | 0.144 |
| 147 | Galβ1-4(6-O-Su)GlcNAcβ-sp3 | 0.003 | 0.162 | 0.380 |
| 150 | 3-O-Su-Galβ1-3GalNAcα-sp3 | 0.003 | 0.146 | 0.372 |
| 151 | 6-O-Su-Galβ1-3GalNAcα-sp3 | 0.009 | 0.118 | 1.387 |
| 152 | 3-O-Su-Galβ1-4Glcβ-sp2 | 0.008 | 0.360 | 0.086 |
| 153 | 6-O-Su-Galβ1-4Glcβ-sp2 | 0.000 | 0.130 | 0.279 |
| 155 | 3-O-Su-Galβ1-3GlcNAcβ-sp3 | −0.014 | 0.219 | 0.838 |
| 157 | 3-O-Su-Galβ1-4GlcNAcβ-sp3 | −0.003 | 0.206 | 0.330 |
| 159 | 4-O-Su-Galβ1-4GlcNAcβ-sp3 | 0.007 | 0.193 | 0.766 |
| 161 | 6-O-Su-Galβ1-3GlcNAcβ-sp3 | 0.004 | 0.129 | 0.146 |
| 163 | 6-O-Su-Galβ1-4GlcNAcβ-sp3 | −0.020 | 0.161 | 0.646 |
| 176 | 3-O-Su-Galβ1-4(6-O-Su)Glcβ-sp2 | −0.007 | 0.110 | 0.102 |
| 177 | 3-O-Su-Galβ1-4(6-O-Su)GlcNAcβ-sp2 | −0.427 | 0.188 | 0.868 |
| 178 | 6-O-Su-Galβ1-4(6-O-Su)Glcβ-sp2 | −0.022 | 0.414 | 0.873 |
| 179 | 6-O-Su-Galβ1-3(6-O-Su)GlcNAcβ-sp2 | 0.884 | 0.166 | 0.076 |
| 180 | 6-O-Su-Galβ1-4(6-O-Su)GlcNAcβ-sp2 | 0.003 | 0.057 | 0.613 |
| 181 | 3,4-O-Su$_2$-Galβ1-4GlcNAcβ-sp3 | −0.002 | 0.140 | 0.301 |
| 182 | 3,6-O-Su$_2$-Galβ1-4GlcNAcβ-sp2 | 0.018 | 0.218 | 0.950 |
| 183 | 4,6-O-Su$_2$-Galβ1-4GlcNAcβ-sp2 | 0.058 | 0.262 | 0.133 |
| 184 | 4,6-O-Su$_2$-Galβ1-4GlcNAcβ-sp3 | −0.003 | 0.396 | 1.760 |
| 189 | 3,6-O-Su$_2$-Galβ1-4(6-O-Su)GlcNAcβ-sp2 | −0.041 | 0.438 | 4.455 |
| 201 | 3,4-O-Su$_2$-Galβ1-4GlcNAcβ-sp3 | −0.009 | 0.112 | 0.885 |
| 203 | Galβ1-4(6-O-Su)GlcNAcβ-sp2 | −0.015 | 0.360 | 3.557 |
| 220 | Galα1-3Galβ1-4Glcβ-sp2 | −0.002 | 0.216 | 0.242 |
| 222 | Galα1-3Galβ1-4GlcNAcβ-sp3 | 0.014 | 0.132 | 0.357 |
| 224 | Galα1-4Galβ1-4Glcβ-sp3 | −0.062 | 0.077 | 0.130 |
| 225 | Galα1-4Galβ1-4GlcNAc-sp2 | 0.020 | 0.218 | 0.936 |
| 228 | Galβ1-2Galα1-4GlcNAcβ-sp4 | −0.075 | 0.091 | 0.678 |
| 229 | Galβ1-3Galβ1-4GlcNAcβ-sp4 | 0.002 | 0.210 | 0.230 |
| 231 | Galβ1-4GlcNAcβ1-3GalNAcα-sp3 | 0.000 | 0.206 | 0.742 |
| 232 | Galβ1-4GlcNAcβ1-6GalNAcα-sp3 | 0.008 | 0.168 | 0.640 |
| 254 | Galβ1-3(GlcNAcβ1-6)GalNAcα-sp3 | −0.007 | 0.285 | 0.832 |
| 262 | Galβ1-3GalNAcβ1-3Gal-sp4 | −0.045 | 0.169 | 0.102 |
| 264 | Galβ1-4Galβ1-4GlcNAc-sp3 | 0.013 | 0.174 | 0.876 |
| 373 | Galα1-3Galβ1-4GlcNAcβ1-3Galβ-sp3 | 0.012 | 0.184 | 0.395 |
| 375 | Galα1-4GlcNAcβ1-3Galβ1-4GlcNAcβ-sp3 | −0.009 | 0.649 | 0.260 |
| 376 | Galβ1-3GlcNAcβ1-3Galβ1-4Glcβ-sp4 | 0.098 | 0.231 | 0.381 |
| 377 | Galβ1-3GlcNAcβ1-3Galβ1-3GlcNAcβ-sp2 | 0.001 | 0.184 | 0.069 |
| 378 | Galβ1-3GlcNAcα1-3Galβ1-4GlcNAcβ-sp3 | −0.001 | 0.214 | 0.824 |
| 379 | Galβ1-3GlcNAcβ1-3Galβ1-4GlcNAcβ-sp3 | −0.014 | 0.251 | 0.434 |
| 380 | Galβ1-3GlcNAcα1-6Galβ1-4GlcNAcβ-sp2 | 0.028 | 0.258 | 0.683 |
| 381 | Galβ1-3GlcNAcβ1-6Galβ1-4GlcNAcβ-sp2 | 0.140 | 0.258 | 0.613 |
| 382 | Galβ1-3GalNAcβ1-4Galβ1-4Glcβ-sp3 | 0.387 | 0.108 | 0.438 |
| 383 | Galβ1-4GlcNAcβ1-3Galβ1-4Glcβ-sp2 | −0.070 | 0.114 | 0.078 |
| 385 | Galβ1-4GlcNAcβ1-3Galβ1-4GlcNAcβ-sp3 | 0.277 | 0.115 | 0.125 |
| 387 | Galβ1-4GlcNAcβ1-6Galβ1-4GlcNAcβ-sp2 | 0.033 | 0.373 | 0.076 |
| 388 | Galβ1-4GlcNAcβ1-6(Galβ1-3)GalNAcα-sp3 | 0.008 | 0.152 | 0.229 |
| 504 | (A-GN-M)$_2$-3,6-M-GN-GNβ-sp4 | −0.006 | 0.280 | 0.821 |
| 1A | Galβ1-3GlcNAc | −0.056 | 0.107 | 0.042 |
| 1B | Galβ1-4GlcNAc | −0.023 | 0.203 | 0.523 |

TABLE 4-continued

| | | Average Fold value above background (Ave background + 3x Standard Error of the Mean) | | |
|---|---|---|---|---|
| Number | Structure | SubB WT | SubBΔS106/ ΔT107 | SubBS106A/ T107A |
| 1C | Galβ1-4Gal | −0.022 | 0.199 | 0.458 |
| 1D | Galβ1-6GlcNAc | −0.020 | 0.352 | 0.398 |
| 1E | Galβ1-3GalNAc | −0.013 | 0.178 | 0.775 |
| 1F | Galβ1-3GalNAcβ1-4Galβ1-4Glc | 0.081 | 0.395 | −0.131 |
| 1G | Galβ1-3GlcNAcβ1-3Galβ1-4Glc | 0.031- | 0.114 | 0.091 |
| 1H | Galβ1-4GlcNAcβ1-3Galβ1-4Glc | 0.006 | 0.148 | 0.802 |
| 1I | Galβ1-4GlcNAcβ1-6(Galβ1-4GlcNAcβ1-3)Galβ1-4Glc | 0.070 | 0.220 | 0.282 |
| 1J | Galβ1-4GlcNAcβ1-6(Galβ1-3GlaNAcβ1-3)Galβ1-4Glc | 0.004 | 0.273 | 0.646 |
| 1K | Galα1-4Galβ1-4Glc | −0.026 | 0.121 | 0.299 |
| 1L | GalNAcα1-O-Ser | −0.002 | 0.662 | 0.098 |
| 1M | Galb1-3GalNAcα1-O-Ser | 0.030 | 0.192 | −0.725 |
| 1N | Galα1-3Gal | −0.026 | 0.308 | 0.618 |
| 1O | Galα1-3Galβ1-4GlcNAc | −0.003 | 0.217 | 0.103 |
| 1P | Galα1-3Galβ1-4Glc | −0.010 | 0.291 | 0.844 |
| 2A | Galα1-3Galβ1-4Galα1-3Gal | 0.089 | 0.159 | 0.609 |
| 2B | Galβ1-6Gal | 0.321 | 0.104 | 0.136 |
| 2C | GalNAcβ1-3Gal | 0.000 | 0.326 | 0.899 |
| 2D | GalNAcβ1-4Gal | 0.045 | 0.125 | 0.667 |
| 2E | Galα1-4Galβ1-4GlcNAc | 0.017 | 0.524 | 0.023 |
| 2F | GalNAcα1-3Galβ1-4Glc | −0.004 | 0.324 | 0.386 |
| 2G | Galβ1-3GlcNAcβ1-3Galβ1-4GlcNAcβ1-6(Galβ1-3GlcNAcβ1-3)Galβ1-4Glc | −0.001 | 0.113 | 0.750 |
| 2H | Galβ1-3GlcNAcβ1-3Galβ1-4GlcNAcβ1-3Galβ1-4Glc | −0.075 | 0.100 | 0.559 |
| 18B | Galβ1-3GalNAcβ1-3Galα1-4Galβ1-4Glc | −0.016 | 0.142 | 0.757 |
| 18C | Galβ1-3GalNAcβ1-3Gal | 0.091 | 0.208 | 0.659 |
| 18L | Galβ1-4Glc | −0.035 | 0.201 | 0.201 |
| 18M | Galβ1-4Gal | 0.011 | 0.382 | 0.493 |
| 18N | Galβ1-6Gal | 0.000 | 0.093 | 0.185 |
| | Terminal N-Acetylgalactosamine | | | |
| 101 | GalNAcα1-3GalNAcβ-sp3 | 0.015 | 0.148 | 0.015 |
| 102 | GalNAcα1-3Galβ-sp3 | −0.012 | 0.103 | 0.396 |
| 103 | GalNAcα1-3GalNAcα-sp3 | −0.007 | 0.177 | 0.087 |
| 104 | GalNAcβ1-3Galβ-sp3 | 0.000 | 0.139 | 0.050 |
| 106 | GalNAcβ1-4GlcNAcβ-sp3 | −0.031 | 0.062 | 0.427 |
| 192 | GalNAcβ1-4(6-O-Su)GlcNAcβ-sp3 | −0.196 | 0.203 | 0.049 |
| 193 | 3-O-Su-GalNAcβ1-4GlcNAcβ-sp3 | −0.253 | 0.175 | 0.161 |
| 194 | 6-O-Su-GalNAcβ1-4GlcNAcβ-sp3 | 0.000 | 0.105 | 0.077 |
| 195 | 6-O-Su-GalNAcβ1-4-(3-O-Su)GlcNAcβ-sp3 | −0.009 | 0.292 | −0.009 |
| 196 | 3-O-Su-GalNAcβ1-4(3-O-Su)-GlcNAcβ-sp3 | −0.028 | 0.148 | 0.810 |
| 197 | 3,6-O-Su$_2$-GalNAcβ1-4GlcNAcβ-sp3 | −0.021 | 0.210 | 0.116 |
| 198 | 4,6-O-Su$_2$-GalNAcβ1-4GlcNAcβ-sp3 | −0.004 | 0.203 | 0.123 |
| 199 | 4,6-O-Su$_2$-GalNAcβ1-4-(3-O-Ac)GlcNAcβ-sp3 | −0.300 | 0.347 | 0.834 |
| 200 | 4-O-Su-GalNAcβ1-4GlcNAcβ-sp3 | 0.000 | 0.108 | 0.109 |
| 202 | 6-O-Su-GalNAcβ1-4(6-O-Su)GlcNAcβ-sp3 | 0.332 | 0.125 | 0.073 |
| 204 | 4-O-Su-GalNAcβ1-4GlcNAcβ-sp2 | 0.262 | 0.115 | 0.503 |
| 238 | GalNAcβ1-4Galβ1-4Glcβ-sp3 | −0.005 | 0.148 | 0.560 |
| 389 | GalNAcβ1-3Galα1-4Galβ1-4Glcβ-sp3 | −0.018 | 0.127 | 0.044 |
| 1L | GalNAcα1-O-Ser | 0.022 | 0.175 | 0.052 |
| 2C | GalNAcβ1-3Gal | −0.009 | 0.142 | 0.070 |
| 2D | GalNAcβ1-4Gal | 0.094 | 0.112 | 0.049 |
| 2F | GalNAcα1-3Galβ1-4Glc | 0.000 | 0.125 | 0.145 |
| | Fucosylated | | | |
| 71 | Fucα1-2Galβ-sp3 | −0.075 | 0.272 | 0.066 |
| 72 | Fucα1-3GlcNAcβ-sp3 | −0.262 | 0.077 | 0.114 |
| 73 | Fucα1-4GlcNAcβ-sp3 | −0.014 | 0.128 | 0.104 |
| 215 | Fucα1-2Galβ1-3GlcNAcβ-sp3 | −0.018 | 0.228 | 0.095 |
| 216 | Fucα1-2Galβ1-4GlcNAcβ-sp3 | 0.029 | 0.166 | 0.154 |
| 217 | Fucα1-2Galβ1-3GalNAcα-sp3 | 0.007 | 0.159 | 0.206 |
| 219 | Fucα1-2Galβ1-4Glcβ-sp4 | 0.000 | 0.136 | 0.145 |
| 226 | Fucα1-2(Galα1-3)Galβ-sp3 | 0.000 | 0.150 | 0.067 |
| 233 | Galβ1-3(Fucα1-4)GlcNAcβ-sp3 | 0.000 | 0.140 | 0.437 |
| 234 | Fucα1-3(Galβ1-4)GlcNAcβ-sp3 | −0.325 | 0.109 | 0.677 |
| 235 | Fucα1-2(GalNAcα1-3)Galβ-sp3 | 0.006 | 0.260 | 0.433 |
| 287 | 3-O-Su-Galβ1-3(Fucα1-4)GlcNAcβ-sp3 | −0.029 | 0.125 | 0.507 |
| 288 | Fucα1-3(3-O-Su-Galβ1-4)GlcNAcβ-sp3 | −0.007 | 0.268 | 0.546 |
| 359 | Fucα1-2(Galα1-3)Galβ1-3GlcNAcβ-sp3 | 0.738 | 0.343 | 0.102 |
| 360 | Fucα1-2(Galα1-3)Galβ1-4GlcNAcβ-sp3 | 0.000 | 0.147 | 0.126 |
| 362 | Fucα1-2(Galα1-3)Galβ1-3GalNAcα-sp3 | −0.403 | 0.298 | 0.249 |
| 363 | Fucα1-2(Galα1-3)Galβ1-3 GalNAcβ-sp3 | −0.029 | 0.140 | 0.269 |
| 364 | Fucα1-3(Galα1-3Galβ1-4)GlcNAcβ-sp3 | 0.354 | 0.106 | 0.995 |
| 366 | Fucα1-2(GalNAcα1-3)Galβ1-3GlcNAcβ-sp3 | 0.022 | 0.160 | 0.418 |

TABLE 4-continued

| Number | Structure | SubB WT | SubBΔS106/ΔT107 | SubBS106A/T107A |
|---|---|---|---|---|
| 368 | Fucα1-2(GalNAcα1-3)Galβ1-4GlcNAcβ-sp3 | 0.003 | 0.106 | 0.283 |
| 371 | Fucα1-2(Galβ1-3(Fucα1-4)GlcNAcβ-sp3 | −0.002 | 0.307 | 0.195 |
| 372 | Fucα1-3(Fucα1-2Galβ1-4)GlcNAcβ-sp3 | 0.085 | 0.917 | 0.190 |
| 392 | Fucα1-2(GalNAcα1-3)Galβ1-3GalNAcα-sp3 | −0.166 | 0.145 | 0.125 |
| 479 | Fucα1-2Galβ1-3GlcNAcβ1-3Galβ1-4Glcβ-sp4 | −0.022 | 0.344 | 0.329 |
| 480 | Fucα1-3Galβ1-3GlcNAcβ1-3Galβ1-4GlcNAcβ-sp2 | −0.120 | 0.093 | 0.107 |
| 483 | Fucα1-3(Fucα1-2 (Galα1-3)Galβ1-4)GlcNAcβ-sp3 | 0.000 | 0.116 | 0.070 |
| 496 | Fucα1-2Galβ1-3(Fucα1-4)GlcNAcβ1-3Galβ1-4Glcβ-sp4 | −0.013 | 0.330 | 0.159 |
| 497 | Fucα1-3(Fucα1-2Galβ1-4)GlcNAcβ1-3Galβ1-4Glcβ-sp4 | −0.012 | 0.177 | 0.086 |
| 538 | Le$^x$1-6' (Le$^c$1-3')Lac-sp4 | 0.003 | 0.096 | 0.153 |
| 539 | LacNAc1-6' (Le$^d$1-3')Lac-sp4 | 0.000 | 0.135 | 0.177 |
| 541 | Le$^x$1-6'(Le$^d$1-3')Lac-sp4 | −0.101 | 0.222 | 0.061 |
| 542 | Le$^c$Le$^x$1-6'(Le$^c$1-3')Lac-sp4 | 0.000 | 0.133 | 0.115 |
| 543 | Le$^x$1-6'(Le$^b$1-3')Lac-sp4 | 0.415 | 0.128 | 0.309 |
| 7A | Fucα1-2Galβ1-3GlcNAcβ1-3Galβ1-4Glc | −0.225 | 0.173 | 0.152 |
| 7B | Galβ1-3(Fucα1-4)GlcNAcβ1-3Galβ1-4Glc | 0.017 | 0.151 | 0.006 |
| 7C | Galβ1-4(Fucα1-3)GlcNAcβ1-3Galβ1-4Glc | 0.001 | 0.255 | 0.305 |
| 7D | Fucα1-2Galβ1-3(Fucα1-4)GlcNAcβ1-3Galβ1-4Glc | 0.002 | 0.160 | −0.029 |
| 7E | Galβ1-4(Fucα1-4)GlcNAcβ1-3Galβ1-4(Fucα1-3)Glc | 0.000 | 0.120 | 0.114 |
| 7F | Fucα1-2Gal | −0.217 | 0.117 | −0.589 |
| 7G | Fucα1-2Galβ1-4Glc | 0.409 | 0.154 | 0.452 |
| 7H | Galβ1-4 (Fucα1-3)Glc | −0.009 | 0.109 | 0.356 |
| 7I | Galβ1-4(Fucα1-3)GlcNAc | −0.002 | 0.227 | 0.370 |
| 7J | Galβ1-3(Fucα1-4)GlcNAc | −0.010 | 0.199 | 0.991 |
| 7K | GalNAcα1-3(Fucα1-2)Gal | 0.016 | 0.360 | 0.343 |
| 7L | Fucα1-2Galβ1-4(Fucα1-3)Glc | −0.012 | 0.165 | 0.502 |
| 7M | Galβ1-3(Fucα1-2)Gal | 0.030 | 0.832 | 0.106 |
| 7N | Fucα1-2Galβ1-4(Fucα1-3)GlcNAc | 0.012 | 0.170 | 0.151 |
| 7O | Fucα1-2Galβ1-3GlcNAc | −0.003 | 0.342 | 0.372 |
| 7P | Fucα1-2Galβ1-3(Fucα1-4)GlcNAc | 0.008 | 0.223 | 0.347 |
| 8A | SO$_3$-3Galβ1-3(Fucα1-4)GlcNAc | 0.011 | 0.169 | 0.636 |
| 8B | SO$_3$-3Galβ1-4(Fucα1-3)GlcNAc | 0.024 | 0.192 | 0.660 |
| 8C | Galβ1-3GlcNAcβ1-3Galβ1-4(Fucα1-3)GlcNAcβ1-3Galβ1-4Glc | 0.004 | 0.104 | 0.337 |
| 8D | Galβ1-4(Fucα1-3)GlcNAcβ1-6(Galβ1-3GlcNAcβ1-3)Galβ1-4Glc | 0.005 | 0.266 | 0.990 |
| 8E | Galβ1-4(Fucα1-3)GlcNAcβ1-6(Fucα1-2Galβ1-3GlcNAcβ1-3)Galβ1-4Glc | 0.004 | 0.309 | 0.522 |
| 8F | Galβ1-4(Fucα1-3)GlcNAcβ1-6(Fucα1-2Galβ1-3(Fucα1-4)GlcNAcβ1-3)Galβ1-4Glc | 0.012 | 0.445 | 0.265 |
| 8G | Galβ1-4GlcNAcβ1-3Galβ1-4(Fucα1-3)Glc | 0.016 | 0.183 | −0.019 |
| 8H | Fucα1-2Galβ1-4(Fucα1-3)GlcNAcβ1-3Galβ1-4Glc | 0.013 | 0.690 | 0.314 |
| 8I | Fucα1-3Galβ1-4GlcNAcβ1-3Galβ1-4(Fucα1-3)Glc | 0.008 | 0.243 | 0.277 |
| 8J | Fucα1-2Galβ1-4(Fucα1-3)GlcNAcb1-3(Fucα1-2)Galb1-4Glc | 0.011 | 0.133 | 0.674 |
| 8K | Galβ1-4 (Fucα1-3)GlcNAcβ1-6(Galβ1-4GlcNAcβ1-3)Galβ1-4Glc | 0.023 | 0.243 | 0.429 |
| 8L | Galb1-4(Fucα1-3)GlcNAcb1-6(Galb1-4(Fucα1-3)GlcNAcb1-3)Galb1-4Glc | 0.020 | 0.216 | 0.118 |
| 8M | Fuca1-2Galb1-4(Fuca1-3)GlcNAcb1-6(Galb1-4GlcNAcb1-3)Galb1-4Glc | 0.001 | 0.934 | 0.738 |
| 8N | Galb1-3GlcNAcb1-3Galb1-4(Fuca1-3)GlcNAcb1-6(Galb1-3GlcNAcb1-3)Galb1-4Glc | 0.022 | 0.868 | 0.750 |
| 8O | Fucα1-2Galβ1-3GlcNAcβ1-3Galβb1-4(Fucα1-3)GlcNAcβ1-6(Galβ1-3GlcNAcβ1-3)Galβ1-4Glc | 0.000 | 0.176 | 0.256 |
| 8P | GalNAcb1-3(Fuca1-2)Galb1-4Glc | 0.006 | 0.200 | 0.389 |
| 9A | Galb1-3(Fuca1-2)Galb1-4(Fuca1-3)Glc | 0.007 | 0.563 | 0.283 |
| 9B | Galβ1-4GlcNAcβ1-6(Fucα1-2Galβ1-3GlcNAcβ1-3)Galβ1-4Glc | −0.008 | 0.161 | 0.186 |
| 18D | Galα1-3(Fucα1-2)Galβ1-4Glc | −0.004 | 0.259 | 0.459 |
| 18E | GalNAcα1-3(Fucα1-2)Galβ1-4(Fucα1-3)Glc | 0.002 | 0.116 | 0.149 |
| 19J | Galβ1-4(Fucα1-3)GlcNAcβ1-3Gal | 0.004 | 0.183 | 0.181 |
| 19L | Fucα1-2Galβ1-4 (Fucα1-3)GlcNAcβ1-3Gal | 0.018 | 0.342 | 0.370 |
| 19M | Galβ1-3(Fucα1-4)GlcNAcβ1-3Gal | 0.018 | 0.193 | 0.453 |
| 19N | Fucα1-2Galβ1-3(Fucα1-4)GlcNAcβ1-3Gal | 0.004 | 0.729 | 0.182 |
| Sialylated | | | | |
| 169 | Neu5Acα2-3Galβ-sp3 | −0.023 | 0.304 | 0.891 |
| 170 | Neu5Acα2-6Galβ-sp3 | 0.018 | 0.132 | 0.861 |
| 171 | Neu5Acα2-3GalNAcα-sp3 | −0.030 | 0.174 | 0.987 |
| 172 | Neu5Acα2-6GalNAcα-sp3 | −0.003 | 0.649 | 0.992 |
| 174 | Neu5Gcα2-6GalNAcα-sp3 | 0.004 | 0.269 | 0.940 |
| 186 | Neu5Acα2-8Neu5Acα2-sp3 | 0.031 | 0.632 | 0.911 |
| 205 | Neu5Acα2-6GalNAcβ-sp3 | 0.022 | 0.246 | 0.910 |
| 206 | Neu5Gcα2-3Gal-sp3 | 3.339 | 1.190 | 3.798 |
| 289 | Galα1-3(Neu5Acα2-6)GalNAcα-sp3 | 0.009 | 0.454 | 0.809 |
| 290 | Galβ1-3(Neu5Acα2-6)GalNAcα-sp3 | −0.008 | 0.150 | 0.559 |
| 292 | Neu5Acα2-3Galβ1-3GalNAcα-sp3 | 0.002 | 0.231 | 1.006 |
| 293 | Neu5Acα2-3Galβ1-4Glcβ-sp3 | 0.005 | 0.151 | 0.631 |
| 294 | Neu5Acα2-3Galβ1-4Glcβ-sp4 | −0.001 | 0.330 | 0.408 |
| 295 | Neu5Acα2-6Galβ1-4Glcβ-sp2 | −0.015 | 0.286 | 0.033 |

TABLE 4-continued

| Number | Structure | SubB WT | SubBΔS106/ΔT107 | SubBS106A/T107A |
|---|---|---|---|---|
| 298 | Neu5Acα2-3Galβ1-4GlcNAcβ-sp3 | 1.248 | 0.255 | 0.278 |
| 299 | Neu5Acα2-3Galβ1-3GlcNAcβ-sp3 | 0.006 | 0.266 | 0.816 |
| 300 | Neu5Acα2-6Galβ1-4GlcNAcβ-sp3 | 0.000 | 0.308 | 0.478 |
| 303 | Neu5Gcα2-3Galβ1-4GlcNAcβ-sp3 | 2.522 | 1.838 | 3.094 |
| 304 | Neu5Gcα2-6Galβ1-4GlcNAcβ-sp3 | 0.000 | 1.125 | 2.798 |
| 306 | 9-NAc-Neu5Acα2-6Galβ1-4GlcNAcβ-sp3 | −0.005 | 0.129 | 0.261 |
| 315 | Neu5Acα2-3Galβ1-4-(6-O-Su)GlcNAcβ-sp3 | −0.003 | 0.459 | 0.980 |
| 317 | Neu5Acα2-3Galβ1-3-(6-O-Su)GalNAcβ-sp3 | 0.007 | 0.201 | 0.019 |
| 318 | Neu5Acα2-6Galβ1-4-(6-O-Su)GlcNAcβ-sp3 | 0.037 | 0.182 | 0.125 |
| 319 | Neu5Acα2-3-(6-O-Su)Galβ1-4GlcNAcβ-sp3 | 0.000 | 0.559 | 0.105 |
| 321 | (Neu5Acα2-8)₃-sp3 | 0.017 | 0.198 | 0.399 |
| 323 | Neu5Acα2-6Galβ1-3GlcNAc-sp3 | 0.126 | 0.166 | 0.116 |
| 324 | Neu5Acα2-6Galβ1-3(6-O-Su)GlcNAc-sp3 | −0.295 | 0.160 | 0.071 |
| 331 | Neu5Gcα2-3Galβ1-3GlcNAc-sp3 | 0.316 | 1.081 | 1.703 |
| 421 | Neu5Acα2-3(GalNAcβ1-4)Galβ1-4Glcβ-sp2 | −0.039 | 0.124 | 0.312 |
| 422 | Neu5Acα2-3Galβ1-4GlcNAcβ1-3Galβ-sp3 | −0.005 | 0.194 | 0.068 |
| 423 | Fucα1-3(Neu5Acα2-3Galβ1-4)GlcNAcβ-sp3 | 0.843 | 0.150 | 0.603 |
| 426 | Neu5Acα2-3Galβ1-3(Fucα1-4)GlcNAcβ-sp3 | 0.141 | 0.196 | 0.116 |
| 428 | Fucα1-3(Neu5Acα2-3Galβ1-4)6-O-Su-GlcNAcβ-sp3 | 0.118 | 0.193 | 0.067 |
| 429 | Fucα1-3(Neu5Acα2-3(6-O-Su)Galβ1-4)GlcNAcβ-sp3 | 0.066 | 0.063 | 0.091 |
| 433 | Neu5Acα2-3Galβ1-3(Neu5Acα2-6)GalNAcα-sp3 | 0.753 | 0.143 | 0.132 |
| 434 | Neu5Acα2-8Neu5Acα2-3Galβ1-4Glcβ-sp4 | 0.029 | 0.144 | 0.034 |
| 527 | Neu5Acα2-3Galβ1-4GlcNAcβ1-3Galβ1-4GlcNAcβ-sp2 | 0.401 | 0.088 | 0.377 |
| 528 | Fucα1-3(Neu5Acα2-3 Galβ1-4)GlcNAcβ1-3Galβ-sp3 | 0.769 | 0.103 | 2.216 |
| 529 | Neu5Acα2-6(Galβ1-3)GlcNAcβ1-3Galβ1-4Glcβ-sp4 | 0.098 | 0.082 | 0.111 |
| 531 | GalNAcβ1-4(Neu5Acα2-8Neu5Acα2-3)Galβ1-4Glc-sp2 | −0.021 | 0.114 | 0.072 |
| 532 | Neu5Acα2-8Neu5Acα2-8Neu5Acα2-3Galβ1-4Glc-sp2 | 0.053 | 0.345 | 0.181 |
| 533 | (Neu5Acα2-8)2Neu5Acα2-3(GalNAcβ1-4)Galβ1-4Glc-sp2 | −0.001 | 0.163 | 0.381 |
| 534 | Neu5Acα2-3Galβ1-4GlcNAcβ1-3Galβ1-4GlcNAcβ-sp3 | 0.633 | 0.113 | 0.115 |
| 536 | Neu5Acα2-3Galβ1-3GlcNAcβ1-3Galβ1-4Glcβ-sp4 | 0.028 | 0.126 | 0.260 |
| 537 | Neu5Acα2-3Galβ1-4GlcNAcβ1-3Galβ1-4Glcβ-sp4 | 0.547 | 0.102 | 0.619 |
| 540 | Le^x1-6'(6'SLN1-3')Lac-sp4 | 0.062 | 0.350 | 0.580 |
| 10A | Neu5Acα2-3Galβ1-3(Fucα1-4)GlcNAc | −0.007 | 0.088 | 0.864 |
| 10B | Neu5Acα2-3Galβ1-4(Fucα1-3)GlcNAc | −0.002 | 0.294 | 0.791 |
| 10C | Neu5Acα2-3Galβ1-3GlcNAcβ1-3Galβ1-4Glc | 0.207 | 0.193 | 0.974 |
| 10D | Galβ1-4(Fucα1-3)GlcNAcβ1-6(Neu5Acα2-6Galβ1-4GlcNAcβ1-3)Galβ1-4Glc | 0.024 | 0.156 | 0.628 |
| 10E | Neu5Acα2-3Galβ1-3(Neu5Acα2-6)GalNAc | 0.118 | 0.122 | 0.957 |
| 10H | Neu5Acα2-6Galβ1-3GlcNAcβ1-3Galβ1-4(Fucα1-3)Glc | 0.015 | 0.109 | 0.421 |
| 10I | Galβ1-3GlcNAcβ1-3(Neu5Acα2-6Galβ1-4GlcNAcβ1-6)Galβ1-4Glc | 0.422 | 0.096 | 0.632 |
| 10J | Neu5Acα2-6Galβ1-3GlcNAcβ1-3(Galβ1-4GlcNAcβ1-6)Galβ1-4Glc | 0.246 | 0.097 | 0.915 |
| 10K | Neu5Acα2-3Galβ1-4GlcNAc | 0.021- | 0.129 | 0.758 |
| 10L | Neu5Acα2-6Galβ1-4GlcNAc | 0.384 | 0.186 | 0.753 |
| 10M | Neu5Acα2-3Galβ1-3GlcNAcβ1-3Galβ1-4Glc | 0.047 | 0.411 | 0.795 |
| 10N | Galβ1-3(Neu5Acα2-6)GlcNAcβ1-3Galβ1-4Glc | −0.037 | 0.463 | 0.925 |
| 10O | Neu5Acα2-6Galβ1-4GlcNAcβ1-3Galβ1-4Glc | 0.000 | 0.135 | 0.384 |
| 10P | Neu5Acα2-3Galβ1-3(Neu5Acα2-6)GlcNAcβ1-3Galβ1-4Glc | 0.079 | 0.083 | 0.527 |
| 11A | Neu5Acα2-3Galβ1-4Glc | 0.001 | 0.099 | 0.835 |
| 11B | Neu5Acα2-6Galβ1-4Glc | 0.188 | 0.345 | 0.687 |
| 11C | (Neu5Acα2-8Neu5Ac)n (n < 50) | 0.007 | 0.132 | 0.599 |
| 18A | Neu5Acα2-3Galβ1-4GlcNAcβ1-3Galβ1-4Glc | 1.213 | 0.351 | 0.669 |
| 18K | 9-NAc-Neu5Ac | −0.001 | 0.183 | 0.968 |
| 18O | Neu5Gc | 0.035 | 0.283 | 0.650 |
| 19K | Neu5Acα2-3Galβ1-4(Fucα1-3)GlcNAcβ1-3Gal | 0.009 | 0.124 | 0.851 |

Mannose

| 119 | Manα1-2Manβ-sp4 | 0.015 | 0.105 | 0.086 |
|---|---|---|---|---|
| 120 | Manα1-3Manβ-sp4 | 0.063 | 0.076 | 0.377 |
| 121 | Manα1-4Manβ-sp4 | −0.006 | 0.110 | 0.112 |
| 122 | Manα1-6Manβ-sp4 | 0.426 | 0.133 | 0.065 |
| 123 | Manβ1-4GlcNAcβ-sp4 | 0.035 | 0.233 | 0.213 |
| 124 | Manα1-2Manα-sp4 | 0.033 | 0.119 | 0.058 |
| 258 | Manα1-3(Manα1-6)Manβ-sp4 | 0.039 | 0.663 | 0.291 |
| 495 | Manα1-3(Manα1-3(Manα1-6)Manα1-6)Manβ-sp4 | 0.360 | 0.077 | 0.137 |
| 5A | GlcNAcβ1-2Man | 0.580 | 0.106 | 0.338 |
| 5B | GlcNAcβ1-2Manα1-6(GlcNAcβ1-2Manα1-3)Man | 0.411 | 0.176 | 0.070 |
| 5C | Manα1-2Man | −0.002 | 0.133 | 0.959 |
| 5D | Manα1-3Man | −0.008 | 0.389 | 0.154 |

TABLE 4-continued

| | | | Average Fold value above background (Ave background + 3x Standard Error of the Mean) | |
|---|---|---|---|---|
| Number | Structure | SubB WT | SubBΔS106/ΔT107 | SubBS106A/T107A |
| 5E | Manα1-4Man | 0.021 | 0.384 | 0.407 |
| 5F | Manα1-6Man | 0.007 | 0.220 | 0.306 |
| 5G | Manα1-6(Manα1-3)Man | 0.034 | 0.059 | 0.121 |
| 5H | Manα1-6(Manα1-3)Manα1-6(Manα1-3)Man | −0.001 | 0.207 | 0.019 |
| | Terminal N-Acetylglucosamine | | | |
| 113 | GlcNAcβ1-3GalNAcα-sp3 | 0.000 | 0.146 | 0.060 |
| 114 | GlcNAcβ1-3Manβ-sp4 | 0.186 | 0.267 | 0.018 |
| 115 | GlcNAcβ1-4GlcNAcβ-Asn | −0.008 | 0.232 | −0.007 |
| 117 | GlcNAcβ1-4GlcNAcβ-sp4 | 0.004 | 0.159 | 0.015 |
| 118 | GlcNAcβ1-6GalNAcα-sp3 | −0.005 | 0.132 | 0.146 |
| 149 | GlcNAcβ1-4(6-O-Su)GlcNAcβ-sp2 | 0.006 | 0.138 | 0.483 |
| 167 | GlcNAcβ1-4-[HOOC(CH$_3$)CH]-3-O-GlcNAcβ-sp4 | −0.009 | 0.138 | 0.048 |
| 168 | GlcNAcβ1--[HOOC(CH$_3$)CH]-3-O-GlcNAcβ-L-alanyl-D-1-glutaminyl-L-lysine | −0.001 | 0.118 | 0.096 |
| 246 | GlcNAcβ1-2Galβ1-3GalNAcα-sp3 | −0.006 | 0.080 | 0.414 |
| 247 | GlcNAcβ1-3Galβ1-3GalNAcα-sp3 | −0.015 | 0.126 | 0.341 |
| 248 | GlcNAcβ1-3Galβ1-4Glcβ-sp2 | −0.007 | 0.097 | 0.084 |
| 250 | GlcNAcβ1-3Galβ1-4GlcNAcβ-sp3 | −0.020 | 0.133 | 0.278 |
| 251 | GlcNAcβ1-4Galβ1-4GlcNAcβ-sp2 | −0.002 | 0.071 | 0.210 |
| 252 | GlcNAcβ1-4GlcNAcβ1-4GlcNAcβ-sp4 | −0.001 | 0.103 | 0.351 |
| 253 | GlcNAcβ1-6Galβ1-4GlcNAcβ-sp2 | −0.005 | 0.103 | 0.102 |
| 255 | GlcNAcβ1-3(GlcNAcβ1-6)GalNAcα-sp3 | −0.009 | 0.123 | 0.003 |
| 395 | GlcNAcβ1-3(GlcNAcβ1-6)Galβ1-4GlcNAcβ-sp3 | −0.012 | 0.225 | 0.746 |
| 493 | (GlcNAcβ1-4)$_5$β-sp4 | −0.015 | 0.067 | 0.076 |
| 503 | (GlcNAcβ1-4)$_6$β-sp4 | −0.005 | 0.124 | 0.175 |
| 505 | (GN-M)$_2$-3,6-M-GN-GNβ-sp4 | −0.007 | 0.129 | 0.091 |
| 4A | GlcNAcβ1-4GlcNAc | 0.007 | 0.189 | 0.150 |
| 4B | GlcNAcβ1-4GlcNAcβ1-4GlcNAc | 0.001 | 0.230 | 0.511 |
| 4C | GlcNAcβ1-4GlcNAcβ1-4GlcNAcβ1-4GlcNAc | 0.003 | 0.096 | 0.062 |
| 4D | GlcNAcβ1-4GlcNAcβ1-4GlcNAcβ1-4GlcNAcβ1-4GlcNAc | −0.001 | 0.113 | 0.227 |
| 4E | Bacterial cell wall muramyl discaccharide | −0.009 | 0.089 | 0.045 |
| 4F | GlcNAcβ1-4GlcNAcβ1-4GlcNAcβ1-4GlcNAcβ1-4GlcNAc | −0.010 | 0.071 | 0.051 |
| 18G | 6-O-Su-GlcNAc | 0.002 | 0.190 | 0.046 |
| 18H | GlcNAc | 0.014 | 0.184 | 0.591 |
| | Glucose | | | |
| 110 | Glcα1-4Glcβ-sp3 | −0.016 | 0.065 | 0.121 |
| 111 | Glcβ1-4Glcβ-sp4 | −0.005 | 0.114 | 0.089 |
| 112 | Glcβ1-6Glcβ-sp4 | −0.002 | 0.080 | 0.572 |
| 164 | GlcAβ1-3GlcNAcβ-sp3 | −0.010 | 0.136 | 0.564 |
| 165 | GlcAβ1-3Galβ-sp3 | 0.095 | 0.862 | 0.075 |
| 166 | GlcAβ1-6Galβ-sp3 | 0.007 | 0.156 | 0.181 |
| 240 | (Glcα1-4)$_3$β-sp4 | −0.014 | 0.060 | 0.110 |
| 241 | (Glcα1-6)$_3$β-sp4 | −0.007 | 0.144 | 0.507 |
| 390 | (Glcα1-4)$_4$β-5p4 | −0.001 | 0.104 | 0.069 |
| 391 | (Glcα1-6)$_4$β-5p4 | −0.016 | 0.130 | 0.094 |
| 492 | (Glcα1-6)$_5$β-sp4 | 0.029 | 0.102 | 0.451 |
| 502 | (Glcα1-6)$_6$β-sp4 | −0.017 | 0.135 | 0.229 |
| 18I | GlcA | −0.005 | 0.193 | −0.072 |
| 18J | 6-O-(H$_2$PO$_4$)-Glc | 0.000 | 0.244 | 0.026 |
| 19O | Glcα1-4Glcα1-4 | 0.013 | 0.121 | 0.184 |
| 19P | Glcα1-4Glcα1-4Glcα1-4 | −0.002 | 0.220 | 0.361 |
| | Low molecular weight Carageenan and Glycoaminoglycans (GAGS) | | | |
| 12A | Neocarratetraose-41, 3-di-O-sulphate (Na+) | −0.001 | 0.087 | 0.156 |
| 12B | Neocarratetraose-41-O-sulphate (Na+) | 0.063 | 0.217 | 0.216 |
| 12C | Neocarrahexaose-24,41, 3, 5-tetra-O-sulphate (Na+) | −0.007 | 0.098 | 0.498 |
| 12D | Neocarrahexaose-41, 3, 5-tri-O-sulphate (Na+) | −0.017 | 0.097 | 0.027 |
| 12E | Neocarraoctaose-41, 3, 5, 7-tetra-O-sulphate (Na+) | −0.016 | 0.290 | 0.266 |
| 12F | Neocarradecaose-41, 3, 5, 7, 9-penta-O-sulphate (Na+) | 0.001 | 0.283 | 0.532 |
| 12G | ΔUA-2S-GlcNS-6S | −0.009 | 0.120 | 0.377 |
| 12H | ΔUA-GlucNS-6S | −0.002 | 0.219 | 0.239 |
| 12I | ΔUA-2S-GlucNS | 0.072 | 0.101 | 0.014 |
| 12J | ΔUA-2S-GlcNAc-6S | −0.007 | 0.229 | 0.189 |
| 12K | ΔUA-GlcNAc-6S | 0.017 | 0.146 | 0.031 |
| 12L | ΔUA-2S-GlcNAc | −0.009 | 0.272 | 0.154 |
| 12M | ΔUA-GlcNAc | −0.004 | 0.075 | 0.471 |
| 12N | ΔUA-GalNAc-4S (Delta Di-4S) | −0.001 | 0.125 | 0.166 |
| 12O | ΔUA-GalNAc-6S (Delta Di-6S) | −0.007 | 0.156 | 0.148 |
| 12P | ΔUA-GalNAc-4S,6S (Delta Di-disE) | 0.004 | 0.192 | 0.109 |
| 13A | ΔUA-2S-GalNAc-4S (Delta Di-disB) | −0.002 | 0.599 | 0.064 |
| 13B | ΔUA-2S-GalNAc-6S (Delta Di-disD) | −0.001 | 0.167 | 0.226 |

TABLE 4-continued

| Number | Structure | SubB WT | SubBΔS106/ΔT107 | SubBS106A/T107A |
|---|---|---|---|---|
| | | | Average Fold value above background (Ave background + 3x Standard Error of the Mean) | |
| 13C | ΔUA-2S-GalNAe-4S-6S (Delta Di-tisS) | 0.001 | 0.132 | 0.087 |
| 13D | ΔUA-2S-GalNAe-6S (Delta Di-UA2S) | −0.007 | 0.115 | 0.087 |
| 13E | ΔUA-GlcNAe (Delta Di-HA) | 0.000 | 0.117 | 0.102 |
| 14M | ΔUA→2S-GlcN-6S | −0.147 | 0.092 | 0.125 |
| 14N | ΔUA→GlcN-6S | 0.009 | 0.209 | 0.142 |
| 14O | ΔUA→2S-GlcN | −0.051 | 0.098 | 0.198 |
| 14P | ΔUA→GlcN | 0.027 | 0.100 | 0.232 |
| High molecular weight Carageenan and Glycoaminoglycans (GAGS) | | | | |
| 625 | (GlcAβ1-4GlcNAcβ1-3)8-NH$_2$-ol | −0.012 | 0.143 | 0.418 |
| 13F | (GlcAβ1-3GlcNAcβ1-4)n (n = 4) | −0.011 | 0.143 | 0.048 |
| 13G | (GlcAβ1-3GlcNAcβ1-4)n (n = 8) | −0.009 | 0.151 | 0.178 |
| 13H | (GlcAβ1-3GlcNAcβ1-4)n (n = 10) | −0.003 | 0.160 | 0.494 |
| 13I | (Glcβ1-3GlcNAcGlc-4)n (n = 12) | 0.004 | 0.162 | 0.802 |
| 13J | (GlcA/IdoAα/Glc-4GlcNAcα1-4)n (n = 200) | 0.027 | 0.179 | 1.058 |
| 13K | (GlcA/IdoAβ1-3(±4/6S)GalNAcβ1-4)n (n < 250) | 0.040 | 0.260 | 0.068 |
| 13L | ((±2S)GlcA/IdoAα/b1-3(±4S)GalNAcβ1-4)n (n < 250) | 0.159 | 0.135 | 0.070 |
| 13M | (GlcA/IdoAβ1-3(±6S)GalNAcβ1-4)n (n < 250) | 0.467 | 0.202 | 1.857 |
| 13N | HA-4 10 mM | −0.016 | 0.219 | 0.299 |
| 13O | HA-6 10 mM | −0.009 | 0.455 | 0.446 |
| 13P | HA-8 9.7 mM | −0.004 | 0.598 | 0.446 |
| 14A | HA 10 7.83 mM | 0.006 | 0.094 | −0.004 |
| 14B | HA-12 6.5 mM | 0.290 | 0.101 | 0.005 |
| 14C | HA-14 5.6 mM | −0.012 | 0.132 | 0.030 |
| 14D | HA-16 4.9 mM | −0.002 | 0.133 | 0.048 |
| 14E | HA 30000 da 2.5mg/ml | 0.005 | 0.149 | 0.058 |
| 14F | HA 107000 da 2.5mg/ml | 0.007 | 0.264 | 0.060 |
| 14G | HA 190000 da 2.5 mg/ml | 0.019 | 0.075 | 0.084 |
| 14H | HA 220000 da 2.5 mg/ml | 0.586 | 0.082 | 0.104 |
| 14I | HA 1600000 da 2.5 mg/ml | −0.0005 | 0.087 | 0.105 |
| 14J | Heparin sulfate 5 mg/ml | 0.01278 | 0.093 | 0.106 |
| 14K | β1-3Glucan | 0.00477 | 0.094 | 0.110 |
| Complex N-glycans | | | | |
| 627 | (Sia2-6A-GN-M)$_2$-3,6-M-GN-GN13-sp4 | 0.02051 | 0.095 | 0.112 |
| 19A | Galβ1-4GlcNAcβ1-2Manα1-3(Galβ1-4GlcNAcβ1-2Manα1-6Man)β1-4GlcNAcβ1-4(Fucα1-6)GlcNAc | 0.01818 | 0.098 | 0.113 |
| 19B | Galβ1-4GlcNAcβ1-2(Galβ1-4GlcNAcβ1-4)Manα1-3(Galβ1-4GlcNAcβ1-2(Galβ1-4GlcNAcβ1-4)Manα1-6)Manβ1-4GlcNAcβ1-4GlcNAc | 0.00915 | 0.099 | 0.116 |
| 19C | Neu5Acα2-6Galβ1-4GlcNAcβ1-2Manα1-3(Galβ1-4GlcNAcβ1-2Manα1-6)Manβ1-4GlcNAcβ1-4GlcNAc | 0.00848 | 0.101 | 2.135 |
| 19D | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAc | 0.00745 | 0.103 | 1.151 |
| 19E | Galβ1-4GlcNAcβ1-2Manα1-3(Galβ1-4GlcNAcβ1-2Manα1-6)Manβ1-4GlcNAcβ1-4GlcNAc | 0.00316 | 0.103 | 0.156 |
| 19F | Neu5Acα2-6Galβ1-4GlcNAcβ1-2Manα1-3(Neu5Acα2-6Galβ1-4GlcNAcβ1-2Manα2-6)Manβ1-4GlcNAcβ1-4(Fucα1-6)GlcNAc | 0.00284 | 0.103 | 0.172 |
| 19G | Neu5Acα2-6Galβ1-4GlcNAcβ1-2(Neu5Acα2-6Galβ1-4GlcNAcβ1-4)Manα1-3(Neu5Acα2-6Galβ1-4GlcNAcβ1-2Manα1-6)Manβ1-4GlcNAcβ1-4GlcNAc | 0.00056 | 0.104 | 0.175 |
| 19H | GlcNAcβ1-2(GlcNAcβ1-4)Manα1-3(GlcNAcβ1-2Manα1-6)GlcNAcβ1-4Manβ1-4GlcNAcβ1-4GlcNAc | −1E-05 | 0.105 | 0.175 |

Fold values greater than 1 indicate binding significantly above background.

The invention claimed is:

1. An isolated subtilase cytotoxin B subunit (SubB) protein comprising an amino acid sequence of SEQ ID NO:2, or a fragment, a variant, or a derivative thereof, which comprises a deletion of one or more of the amino acid residues of the amino acid sequence TTSTE (SEQ ID NO: 3) and/or a substitution of one or more of the third, fourth, and fifth amino acid residues of the amino acid sequence TTSTE (SEQ ID NO: 3), and wherein the isolated protein, the fragment, the variant, or the derivative thereof is capable of binding α2-3-linked glycolylneuraminic acid and α2-6-linked N-glycolylneuraminic acid.

2. The isolated SubB protein of claim 1, which comprises a substitution or deletion of at least one of the third or fourth amino acid residues of TTSTE (SEQ ID NO:3).

3. The isolated SubB protein, fragment of claim 2, which further comprises a deletion of the fifth amino acid residue of TTSTE (SEQ ID NO:3).

4. The isolated SubB protein of claim 3, which comprises a deletion of the fourth and fifth amino acid residues of TTSTE (SEQ ID NO: 3).

5. The isolated SubB protein of claim 1, which comprises a deletion of at least one of the third or fourth amino acid residues of TTSTE (SEQ ID NO:3).

6. The isolated SubB protein of claim 1, wherein the isolated SubB protein comprises the amino acid sequence of SEQ ID NO: 1.

7. A composition comprising, the isolated SubB protein of claim 1.

8. An isolated molecular complex comprising the isolated SubB protein of claim 1 and a glycan comprising, α2-3-linked N-glycolylneuraminic acid and/or a α2-6-linked N-glycolylneuraminic acid.

9. The isolated molecular complex of claim 8, Wherein the glycan comprising the α2-3-linked N-glycolylneuraminic acid and/or the α2-6-linked N-glycolylneuraminic acid is from a tumour cell or by a feline blood cell.

10. An isolated nucleic acid encoding the isolated SubB protein of claim 1.

11. A genetic construct comprising the isolated nucleic acid of claim 10.

12. A host cell comprising the genetic construct of claim 11.

13. A method of detecting α2-3-linked N-glycolylneuraminic acid and/or α2-6-linked N-glycolylneuraminic acid, said method including the step of combining:
  (a) the isolated SubB protein of claim 1, or
  (b) a composition comprising the isolated SubB protein of claim 1, with a sample to thereby form a detectable complex comprising said isolated SubB protein and α2-3-linked N-glycolylneuraminic acid and/or α2-6-linked N-glycolylneuraminic acid.

14. The method of claim 13, wherein the α2-3-linked N-glycolylneuraminic acid and/or the α2-6-linked N-glycolylneuraminic acid is from a tumour cell or by a feline blood cell.

15. A method of isolating a glycan comprising α2-3-linked N-glycolylneuraminic acid and/or an α2-6-linked N-glycolylneuraminic acid, the method including the steps of: combining:
  (a) the isolated SubB protein of claim 1; or
  (b) a composition comprising the isolated SubB protein of claim 1, with a sample to thereby form a complex comprising said isolated SubB protein and the glycan comprising the α2-3-linked N-glycolylneuraminic acid and/or α2-6-linked N-glycolylneuraminic acid; and isolating the complex.

16. A method of isolating a cell expressing a glycan comprising α2-3-linked N-glycolylneuraminic acid and/or an α2-6-linked N-glycolylneuraminic acid, said method including the steps of combining:
  (a) the isolated SubB protein of claim 1; or
  (b) a composition comprising the isolated SubB protein of claim 1,
with a sample comprising a cell to thereby form a complex comprising said isolated SubB protein and the glycan comprising the α2-3-linked N-glycolylneuraminic acid and/or α2-6-linked N-glycolylneuraminic acid; and isolating the cell.

* * * * *

UNITED STATES PATENT AND TRADEMARK OFFICE
CERTIFICATE OF CORRECTION

PATENT NO. : 11,371,033 B2
APPLICATION NO. : 16/348732
DATED : June 28, 2022
INVENTOR(S) : Jennings et al.

Page 1 of 1

It is certified that error appears in the above-identified patent and that said Letters Patent is hereby corrected as shown below:

In the Specification

Column 4, Line 26: Please correct "TTSTE" to read --TT<u>STE</u>--

Column 5, Line 13: Please correct "Hex2FlexNAc2NeuAc1NeuGc1" to read --Hex2HexNAc2NeuAc1NeuGc1--

Column 8, Line 13: Please correct "TTSTE" to read --TTS<u>TE</u>--

Column 8, Line 35: Please correct "Neu5Ac-β2-3-lac" to read --Neu5Ac-α2-3-lac--

Column 19, Line 28: Please correct "al-acid" to read --α1-acid--

Column 23, Line 6: Please correct "EZ-LinV" to read --EZ-Link®--

In the Claims

Column 45, Line 20, Claim 1: Please correct "α2-3-linked glycolylneuraminic" to read --α2-3-linked N-glycolylneuraminic--

Column 45, Line 37, Claim 7: Please correct "comprising, the" to read --comprising the--

Column 45, Line 40, Claim 8: Please correct "comprising, α2-3-" to read --comprising α2-3- --

Column 45, Line 43, Claim 9: Please correct "Wherein" to read --wherein--

Signed and Sealed this
First Day of November, 2022

Katherine Kelly Vidal
*Director of the United States Patent and Trademark Office*